(12) United States Patent
Tryggvason et al.

(10) Patent No.: US 8,545,845 B2
(45) Date of Patent: Oct. 1, 2013

(54) ANTIBODIES AGAINST DOMAINS OF LAMININ-332

(76) Inventors: Karl Tryggvason, Djursholm (SE); Sirpa Anne Kristiina Salo, Oulu (FI)

( * ) Notice: Subject to any disclaimer, the term of this patent is extended or adjusted under 35 U.S.C. 154(b) by 121 days.

(21) Appl. No.: 13/060,358

(22) PCT Filed: Jun. 18, 2009

(86) PCT No.: PCT/IB2009/006404
§ 371 (c)(1),
(2), (4) Date: Jun. 17, 2011

(87) PCT Pub. No.: WO2009/153670
PCT Pub. Date: Dec. 23, 2009

(65) Prior Publication Data
US 2011/0243965 A1    Oct. 6, 2011

Related U.S. Application Data

(60) Provisional application No. 61/073,611, filed on Jun. 18, 2008.

(51) Int. Cl.
*A61K 39/395* (2006.01)

(52) U.S. Cl.
USPC ................................. 424/138.1; 530/387.7

(58) Field of Classification Search
None
See application file for complete search history.

(56) References Cited

U.S. PATENT DOCUMENTS

| | | | |
|---|---|---|---|
| 5,660,982 A | 8/1997 | Tryggvason et al. | |
| 6,955,924 B2 | 10/2005 | Tryggvason et al. | |
| 7,323,551 B2 | 1/2008 | Marinkovich | |
| 2004/0120959 A1 | 6/2004 | Tryggvason et al. | |
| 2007/0014788 A1 | 1/2007 | Mathiasen et al. | |
| 2007/0065447 A1 | 3/2007 | Tryggvason et al. | |

FOREIGN PATENT DOCUMENTS

| WO | WO 00/26342 | 5/2000 |
|---|---|---|
| WO | WO 2005/040219 A1 | 5/2005 |
| WO | WO 2005/052003 A2 | 6/2005 |
| WO | WO 2005/052003 A3 | 6/2005 |
| WO | WO 2005/056598 A2 | 6/2005 |
| WO | WO 2005/056598 A3 | 6/2005 |
| WO | WO 2008/005828 A2 | 1/2008 |
| WO | WO 2008/005828 A3 | 1/2008 |
| WO | WO 2009/032224 A2 | 3/2009 |
| WO | WO 2009/032224 A3 | 3/2009 |

OTHER PUBLICATIONS

Akimoto Shingo et al: "Laminin 5 beta3 and gamma2 chains are frequently coexpressed in cancer cells" Pathology International, vol. 54, No. 9, Sep. 2004 , pp. 688-692, XP002568740 ISSN: 1320-5463.
Koshikawa Naohiko et al: "Overexpression of laminin gamma2 Chain monomer in invading gastric carcinoma cells" Cancer Research, American Association for Cancer Research, Baltimore, MD., US, vol. 59, No. 21, Nov. 1, 1999, pp. 5596-5601, XP002214130 ISSN: 0008-5472.
Marinkovich M P et al: "The Anchoring Filament Protein Kalinin Is Synthesized and Secreted as a High Molecular Weight Precursor" Journal of Biological Chemistry, American Society of Biological Biologists, Birmingham, US, vol. 267, No. 25, Jan. 1, 1992 , pp. 17900-17906, XP002341 ISSN: 0021-9258.
Salo Sirpa et al: "Antibodies blocking adhesion and matrix binding domains of laminin-332 inhibit tumor growth and metastasis in vivo" International Journal of Cancer, John Wiley & Sons, Inc, United States, Switzerland, Germany, vol. 125. No. 8, Oct. 15, 2009 , pp. 1814-1825, XP008118794 ISSN: 0020-7136 [retrieved on Apr. 23, 2009].
Tran Mark et al: "Targeting a tumor-specific laminin domain critical for human carcinogenesis" Cancer Research, vol. 68, No. 8, Apr. 2008, pp. 2885-2894, XP002568741 ISSN: 0008-5472.
Aberdan D et al: "Developmental expression of nicein adhesion protein (laminin-5) subunits suggests multiple morphogenic roles," Cell Adhesion and Communication Jun. 1994, vol. 2, No. 2, Jun. 1994, pp. 115-129, XP008118864 ISSN: 1061-5385.
International Search Report and Written Opinion, Date of completion Mar. 1, 2010; Date of mailing Sep. 3, 2010, Authorized officer Vadot, Pierre.

*Primary Examiner* — Sheela J Huff
(74) *Attorney, Agent, or Firm* — Fay Sharpe LLP

(57) ABSTRACT

Antibodies against various domains of laminin-332 are discussed herein. The antibodies reduce the adhesion and matrix binding properties of laminin-332, inhibiting tumor growth and metastasis in vivo. Pharmaceutical compositions and methods of using the antibodies for diagnostic, prophylactic, and/or therapeutic purposes are disclosed.

20 Claims, 10 Drawing Sheets

ANTIBODIES AGAINST DOMAINS OF LAMININ-332

CROSS-REFERENCE TO RELATED APPLICATIONS

This application claims priority to U.S. Provisional Patent Application Ser. No. 61/073,611, filed Jun. 18, 2008, the entirety of which is fully incorporated by reference herein.

BACKGROUND

The present disclosure relates to antibodies capable of selectively binding to various domains on the chains of laminin-332, compositions thereof, and methods of using such antibodies/compositions for various purposes.

Laminins are trimeric basement membrane (BM) glycoproteins with roles in cell adhesion, proliferation, migration and differentiation. The laminin molecule is a cross-shaped heterotrimer consisting of one heavy chain (alpha) and two light chains (beta and gamma). The three chains are associated through a carboxyl terminal coiled coil domain. In addition, all of the alpha chains have a large globular G domain at the carboxyl terminus.

In mammals, five genetically distinct alpha ($\alpha$), three beta ($\beta$), and three gamma ($\gamma$) chains can form at least 14 different combinations of these chains (References 1, 2). Laminin-332 (also denoted as LN-332, also known as laminin-5, LN-5, kalinin, nicein) has a chain composition $\alpha 3:\beta 3:\gamma 2$ (FIG. 8) and is essential for anchorage of epithelial cells and specifically found in epithelial BMs (References 3-5). LN-332 defects lead to detachment of epithelia and the fatal skin blistering disease junctional epidermolysis bullosa (References 6-8). LN-332 also has a role in proliferation and locomotion of epithelial cells, such as in keratinocytes of healing wounds (References 9, 10). The globular domain (G-domain) of the $\alpha_3$ chain binds to the cell surface through integrin receptors $\alpha 6\beta 4$ and $\alpha 3\beta 1$ (Reference 11) and evokes anti-apoptotic signals through focal adhesion kinase (References 12, 13), while the short arms of the $\beta 3$ and $\gamma 2$ chains bind to type VII collagen in the stroma (Reference 14).

LN-332 is up-regulated in various epithelial cancers, including colon, gastric, mammary duct and squamous cell carcinomas, as well as melanomas (References 5-18), but not in mesenchymal cancers (References 15, 16). High expression of the $\gamma 2$ chain of LN-332 has been found to correlate with poor prognosis of cervical squamous cell carcinomas (Reference 19). LN-332 is also a major scattering factor stimulating invasive and metastatic capacity of several tumor cell lines in vitro (References 20, 21). In the cancer tissue, the protein is primarily expressed at the invasive front, as well as in micro-metastases. Down-regulation of LN-332 has been reported in epithelial prostate cancer (Reference 22) and also in breast cancers (Reference 23).

LN-332 expression has been associated with tumorigenesis. Thus, when HT1080 tumor cells constitutively expressing laminin $\beta 3$ and $\gamma 2$ chains but not $\alpha 3$ were transfected with laminin $\alpha 3$ cDNA the cells grew significantly larger tumors in nude mice than untransformed cells (Reference 24). Moreover, LN-332 negative (as well as $\alpha 4$ integrin negative) keratinocytes did not become tumorigenic upon transfection with ras-I$\kappa$B$\alpha$ in contrast to normal keratinocytes (Reference 25).

Since most cancers are of epithelial origin and positive for LN-332 expression, present applicants investigated whether this protein has a general role for the adhesion and migration process of invading carcinoma cells, and if interference with those functions might influence tumor growth and spread. In particular, present applicants studied the role of LN-332 for carcinoma cell adhesion and migration in vitro and demonstrated that interference with the binding of this protein to the cells inhibits these functions and induces apoptosis. Furthermore, present applicants showed that antibodies against the cell and matrix binding domains of LN-332 target to several types of carcinomas growing in vivo and effectively inhibit tumor growth and metastasis in mice.

BRIEF DESCRIPTION

Disclosed in embodiments are various antibody compositions comprising antibodies against the $\beta 3$ chain of laminin-332. The antibodies may specifically bind to domains III-VI on the $\beta 3$ chain.

The antibody composition may further comprise antibodies against the $\gamma 2$ chain of laminin-332. The antibodies against the $\gamma 2$ chain may bind to domain III or domain V on the $\gamma 2$ chain.

Alternatively, the antibody composition may further comprise antibodies against the G domain of the $\alpha 3$ chain of laminin-332. The antibodies against the G domain may bind to subdomains G1-G3 of the $\alpha 3$ chain.

In other embodiments, the antibody composition further comprises both antibodies against the $\gamma 2$ chain of laminin-332 and antibodies against the G domain of the $\alpha 3$ chain of laminin-332.

Also disclosed are methods of decreasing cell migration in cells exhibiting metastasis, comprising contacting cells with antibodies against the $\beta 3$ chain of laminin-332.

Further disclosed are methods of decreasing tumor growth, comprising administering to a subject with a laminin-332 secreting tumor an effective amount of an antibody against the $\beta 3$ chain of laminin-332.

Antibodies against the cell binding domain of the $\alpha 3$ chain of LN-332 inhibited tumor growth by up to 68%, and antibodies against the matrix binding domains of the $\beta 3$ and $\gamma 2$ chains significantly decreased lung metastases. The LN-332 antibodies appear to induce tumor cell anoikis and subsequent programmed cell death. The LN-332 antibodies also reduce migration by interfering with tumor cell matrix interactions, or in other words decrease metastasis by dissociating the cells from the extracellular matrix.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1:
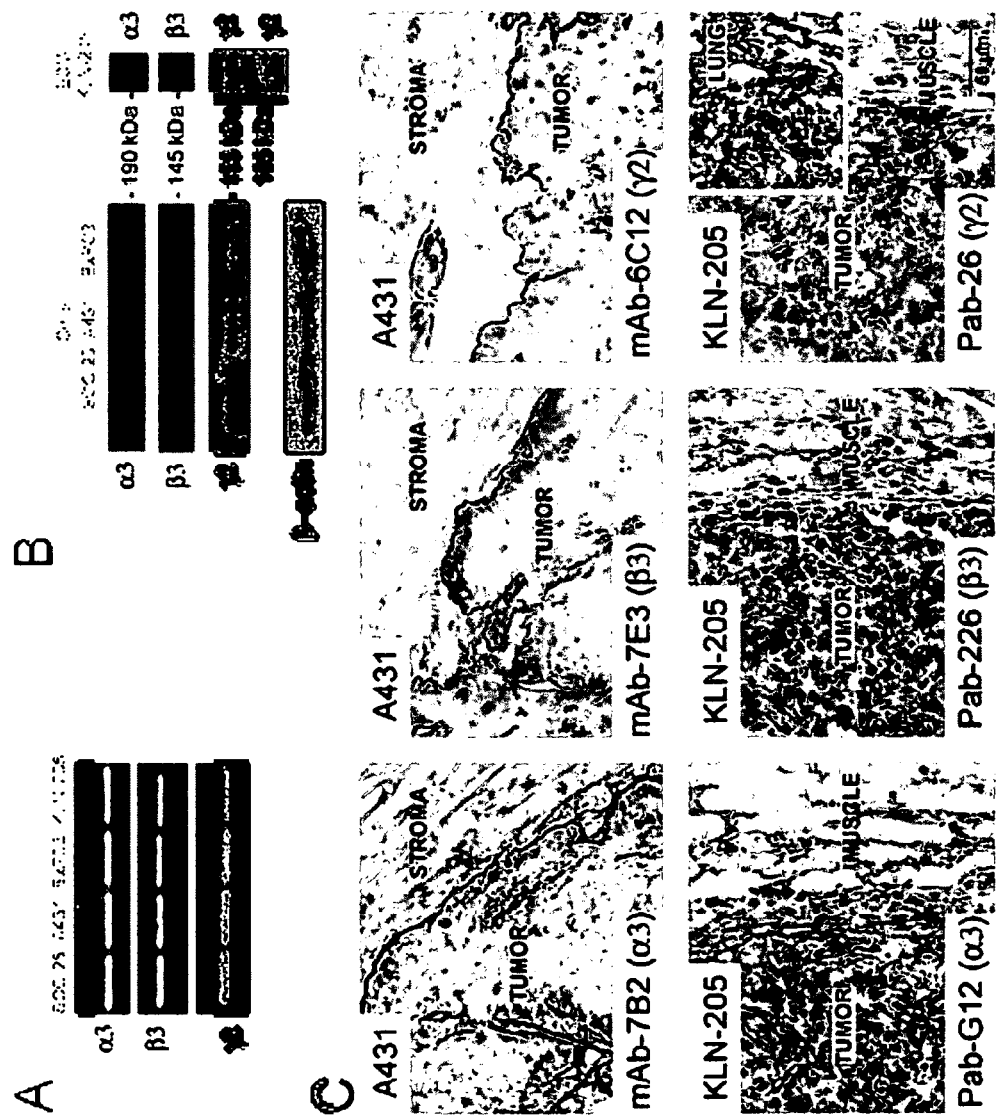
FIG. 1A shows the results of RT-PCR analysis revealing expression of all three LN-332 chains in mouse KLN-205 SCC, and human A431 SCC, SCC-25 and BxPC3 adenocarcinoma cell lines used in this study.
FIG. 1B is a Western blot showing that all three LN-332 component chains are synthesized by the four SCC lines. The secreted $\gamma 2$ chain was partially processed in the culture medium to a smaller 105 kDa form as shown for the KLN-205 cells.
FIG. 1C illustrates three A431 tumors and three mouse KLN-205 tumors using monoclonal antibodies against the three LN-332 chains that show strong peroxidase staining at the invading periphery of the tumor in nude mice. The mouse KLN-205 tumor grown in skeletal muscle is also strongly positive for staining with antibodies against the three chains at the invading front, and lung metastasis is also positive. Magnification 200×.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The present disclosure relates to compositions including antibodies that are useful for inhibiting tumor growth and metastasis by binding to laminin-332. This binding inhibits adhesion and migration of tumor cells, which are dependent upon laminin-332.

An antibody refers to an immunoglobulin (Ig) monomer. Each Ig monomer consists of two heavy chains and two light chains which join together to form a Y-shape. Each Ig monomer can be divided into Fab, F(ab')2, and Fv fragments as is known in the art. The antibody has the ability to bind to a desired antigen under typical physiological conditions for a significant functionally-defined period of time (i.e. a time sufficient to induce, promote, enhance, or modulate a physiological response associated with the binding). The term "antibody" as used herein is intended to refer to an intact antibody molecule, i.e. an Ig monomer, and fragments thereof which are capable of binding an epitope.

Figure 8:
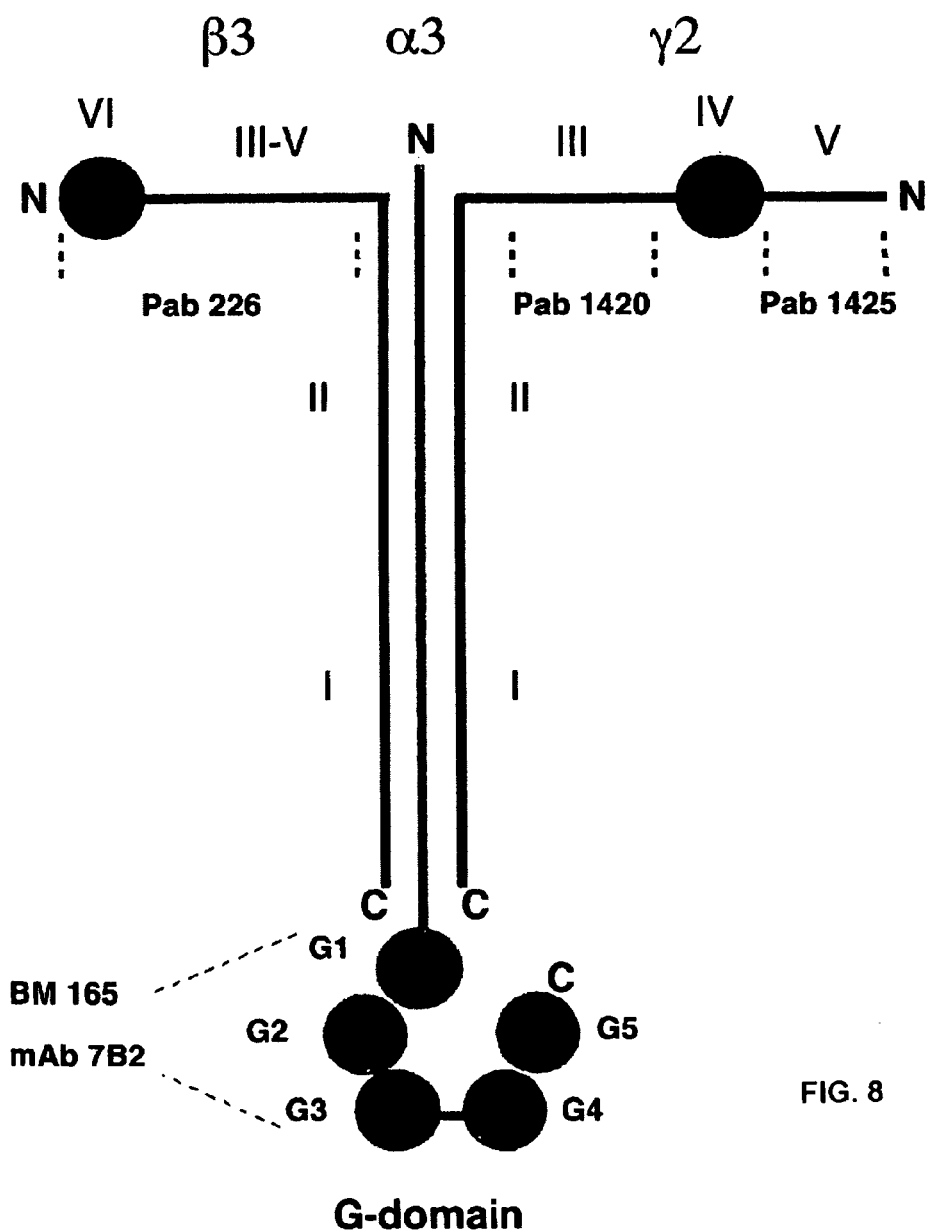
FIG. 8 is a depiction of a laminin molecule. The $\alpha$3, $\beta$3, and 2 chains are shown. C refers to the carboxy terminal, and N refers to the amino terminal. The structural domains of the $\beta$3 and $\gamma$2 chains are shown in Roman numerals, and five subdomains of the G domain of the $\alpha$3 chain are shown. Pab-226 reacted with domains III to VI of the $\beta$3 chain. Pab-1420 reacted with domain III of the $\gamma$2 chain, and Pab-1425 reacted with domain V of the $\gamma$2 chain. mAb-7B2 reacted with the G1-G3 subdomains, and mAb BM165 reacted against the entire G domain. Pab-PST was prepare against the whole trimeric recombinant human LN-332 molecule.

FIG. 8 is an illustration of the laminin-332 molecule and shows the three chains along with labels indicating various domains on each chain. In particular, the domains I and II of all three chains appear to comprise a coiled coil domain structure. Between the coiled coil region of domains II and III are flexible hinge regions.

In embodiments, the antibody composition comprises antibodies against the chains of laminin-332, particularly the $\beta$3 chain of laminin-332. In particular embodiments, the antibodies selectively bind to domains III through VI of the $\beta$3 chain, which are on the amino terminal end of the $\beta$3 chain. Exemplary antibodies discussed in the Examples include Pab-226 and mAb-7E3.

The antibody composition may further comprise antibodies against the $\gamma$2 chain of laminin-332. In particular, these antibodies against the $\gamma$2 chain selectively bind to domain III or domain V on the $\gamma$2 chain. Exemplary antibodies discussed in the Examples include Pab-1420, Pab-1425, 4G1, 6C12, and Pab-26.

The antibody composition may alternatively further comprise antibodies against the G domain of the $\alpha$3 chain of laminin-332. Some of these antibodies against the G domain may selectively bind to subdomains G1-G3 of the $\alpha$3 chain. Exemplary antibodies discussed in the Examples include BM165, RG13, mAb-7B2, and Pab-G12.

In some embodiments, the antibody composition comprises antibodies against the $\beta$3 chain of laminin-332, along with either or both antibodies against the $\gamma$2 chain of laminin-332 and antibodies against the G domain of the $\alpha$3 chain of laminin-332.

Alternatively, the antibody composition comprises antibodies, such as isolated or purified antibodies, against the $\gamma$2 chain of laminin-332.

Alternatively, the antibody composition comprises antibodies, such as isolated or purified antibodies, against the G domain of the $\alpha$3 chain of laminin-332.

The term "selectively bind" refers to the preferential binding of the antibody to one or more epitopes contained in a particular region or target. Generally, the antibody will possess little or no binding or reactivity to other epitopes.

The antibodies against the $\beta$3 chain, the 2 chain, and/or the G domain of the $\alpha$3 chain may each be monoclonal antibodies or polyclonal antibodies. They can be chimeric antibodies, i.e. antibodies formed by combining regions from different antibodies. They may also be humanized, i.e. derived from a non-human species in which certain regions have been mutated to reduce or avoid an immune response in humans. Alternatively, the antibodies can be fully human, i.e. derived from human germ lines. The antibodies may be isolated or purified.

The actual dosage level and the mode of administration of the antibody compositions of this disclosure can be varied in order to achieve the effective therapeutic response for a particular patient. The phrase "therapeutically effective amount" means a sufficient amount of the compound to treat disorders, at a reasonable benefit/risk ratio applicable to any medical treatment. It will be understood, however, that the total daily usage of the antibodies and compositions of the present disclosure will be decided by the attending physician within the scope of sound medical judgment. The total daily dose of the antibody compositions of this disclosure may range from about 0.0001 to about 1000 mg/kg/day. If desired, the effective daily dose can be divided into multiple doses for purposes of administration; consequently, single dose compositions may contain such amounts or submultiples thereof to make up the daily dose. The specific therapeutically effective dose level for any particular patient will depend upon a variety of factors including the disorder being treated and the severity of the disorder; medical history of the patient, activity of the specific compound employed; the specific composition employed, age, body weight, general health, sex and diet of the patient, the time of administration, route of administration, the duration of the treatment, rate of excretion, other drugs used in combination; and the like.

The mode of administration of the antibody compositions of this disclosure can be oral, rectal, intravenous, intramuscular, intracisternal, intravaginal, intraperitoneal, bucal, subcutaneous, intrasternal, nasal, or topical. The compositions can also be delivered at the target site through a catheter, an intracoronary stent (a tubular device composed of a fine wire mesh), a biodegradable polymer, or biological carriers including, but not limited to, antibodies, biotin-avidin complexes, and the like. Dosage forms for topical administration include powders, sprays, ointments and inhalants. The antibodies are mixed under sterile conditions with a pharmaceutically acceptable carrier and any needed preservatives, buffers or propellants. Opthalmic formulations, eye ointments, powders and solutions are also contemplated as being within the scope of this disclosure. Preferably, the antibody compositions are administered intravenously or subcutaneously.

The antibodies may be made up in a solid form (including granules, powders or suppositories) or in a liquid form (e.g., solutions, suspensions, or emulsions). The antibodies may be applied in a variety of solutions. Suitable solutions for use in accordance with the invention are sterile, dissolve sufficient amounts of the antibodies, and are not harmful for the proposed application.

The antibodies may be subjected to conventional pharmaceutical operations such as sterilization and/or may contain conventional adjuvants, such as preservatives, stabilizers, wetting agents, emulsifiers, buffers etc.

For administration, the antibodies can be combined with one or more pharmaceutically acceptable carriers appropriate for the indicated route of administration. The antibodies may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the antibodies may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In other aspects of this disclosure, a method of decreasing cell migration is provided by contacting cells with antibodies against the β3 chain of laminin-332. Preferably, the cells which are contacted are tumor cells or cancer cells. As explained further herein, cells at the invasive front of carcinomas are often positive for LN-332 expression.

In another aspect, a method of decreasing tumor growth is provided, comprising administering to a subject with a laminin-332 secreting tumor an effective amount of an antibody against the β3 chain of laminin-332.

The following examples are for purposes of further illustrating the present disclosure. The examples are merely illustrative and are not intended to limit devices made in accordance with the disclosure to the materials, conditions, or process parameters set forth therein.

Examples

Materials and Methods

Cells. Human epidermoid carcinoma cell line, A431 (cat. no ATCC CRL-1555), human squamous cell carcinoma (SCC) cell line SCC-25 (cat. no ATCC CRL-1628), human adenocarcinoma cell line BxPC3 (cat. no ATCC CRL-1687), human BJ fibroblasts (cat. no ATCC CRL-2522) and mouse SCC cell line KLN-205 (cat. No ATCC CRL-1453) and mouse fibroblasts NIH-3T3 (cat. no ATCC CRL-1658) were obtained from American Type Culture Collection (ATCC). All cells were maintained as monolayer cultures in cell culture media recommended by ATCC. Mouse fibroblasts NIH-3T3 used to study type VII collagen expression were cultured with DMEM supplemented with 10% FBS, antibodies and (+)-sodium L-ascorbate (100 µg/ml, Sigma, USA), an essential cofactor for collagen prolyl and lysyl hydroxylases.

Proteins and antibodies. Recombinant LN-332 (rLN-332), recombinant laminin α3 G-domain fragments G12 (rG12) and G123 (rG123) and recombinant laminin β3 short-arm 65 kD fragment (rβ3-65 kD) were obtained from BioStratum, Inc., USA (U.S. Pat. No. 6,703,363, see Supplemental Materials and Methods).

Figure 9:
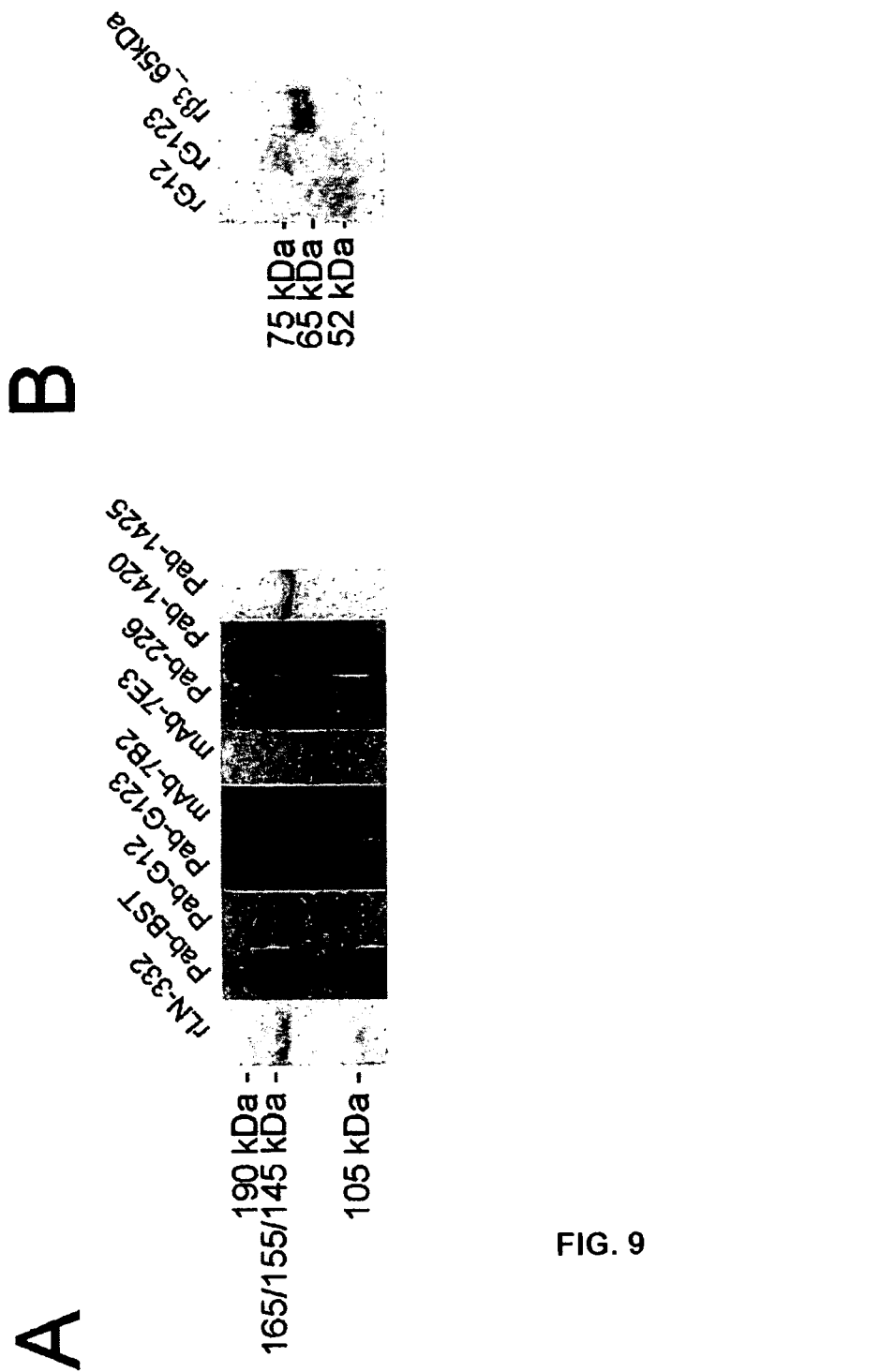
FIG. 9A is an immunoblot characterization of new polyclonal and monoclonal antibodies used in this study. Recombinant LN-332 (rLN-332) was loaded on 6% SDS-PAGE and immunoblotted. Pab BST prepared against trimeric LN-332 reacts with all three chains. Pab-G12, Pab-G123 and mAb-7B2 made against the G domain of $\alpha$3 chain recognize both unprocessed and processed forms of the chain. mAb-7E3 and Pab-226 are specific for the $\beta$3 chain. Polyclonal antibodies made against domain III of the $\gamma$2 chain (Pab-1420) recognizes both unprocessed and processed forms of the chain, while Pab-1425 directed against domain V of the $\gamma$2 chain only recognizes the unprocessed form.
FIG. 9B is an SDS-PAGE (10%) analysis of new recombinant G12, G123 and $\beta$3 65 kD fragments. 5 µg of each protein was loaded/well. Coomassie blue staining.

Polyclonal antibodies were generated against a part of domain III of murine γ2 (Pab-1420), and a part of domain V (Pab-1425) (see FIG. 8). Monoclonal antibody (mAb) 4G1 was obtained from DAKO, Denmark (M7262) and monoclonal antibody 6C12 has been characterized previously (Reference 26). mAb BM165 (Reference 27) was a kind gift from Paul F. Goetinck, and mAbs CM6 and RG13 (References 28 and 29), were a kind gift from Jonathan Jones. MAb-7B2 and mAb-7E3 were produced against rLN-332 using traditional hybridoma techniques. The hybridomas were characterized using ELISA, immunohistochemistry and western analysis (see FIG. 9). Polyclonal antibody Pab-26 (Pab γ2III) has been characterized previously (References 16 and 19). Polyclonal antibody Pab-BST was raised against the rLN-332, Pab-G12 against the G-domain fragment rG12 and Pab-226 against the β3-short arm fragment rβ3 65 kD in rabbits and characterized using ELISA, immunohistochemistry and Western analysis (FIG. 9).

Cell adhesion assays. 96-well microtiter plates (Maxi-Sorpt™, Nunc) were coated with 0.1 µg/well of rLN-332 in phosphate-buffered saline (PBS) and potential active binding sites were blocked with 200 µg/well 1% bovine serum albumin (BSA). A total of 20,000-25,000 A431, SCC-25 or BxPC3 cells were plated in 100 µl to each well and allowed to attach for 2 hours at 37° C., and then fixed with 4% paraformaldehyde and stained with 0.1% crystal violet. All antibodies and controls were tested in triplicates wells.

RealTime Cell Electronic Sensing (RT-CES™) technology (ACEA Biosciences Inc., San Diego, Calif., (30) was used to assess cell adhesion and the inhibitory effect of antibodies more accurately. The ACEA E-plates were coated with 5 μg/ml of rLN-332 for 1 hour at 37° C., washed with PBS and potential remaining active sites were blocked with 0.5% BSA in PBS. The wells were washed with PBS and 25 000 cells/well were added with or without various concentrations of mAb 7B2 or BM165. Cell Index (Reference 31) was measured continuously in the following hours.

Migration Assays.

For studies of cell migration on plastic, flat-bottomed 24-well cell culture plates (Corning) were seeded with $2\times10^5$ cells/well of SCC-25 or BxPC3 cells and cultured overnight. Cells were then treated with 10 μg/ml Mitomycin C (Sigma) for 2 hours at 37° C. after which the cell layers were wounded by scratching the cell layer with a pipet tip. The wound size was measured under a microscope and the most similar wounds were chosen for the assay. For inhibition assay of cell migration, medium containing 10% FCS was added to the wells with or without antibodies and controls (50 μg/ml). All cells treated with control antibodies or without antibody treatments were able to migrate properly after Mitomycin C treatment confirming that Mitomycin C itself did not affect cell migration. The cells were allowed to migrate for 20 hours at 37° C., stained with Diff-Quick (Dade) and the wounds were measured and photographed (Leica MZFL111).

For studies of migration of KLN-205 cells on extracellular matrix produced by fibroblasts, flat-bottomed 24-well cell culture plates (Corning) were seeded with $2\times10^5$ cells/well of mouse NIH-3T3 cells and cultured to confluency overnight. Extracellular fibroblast matrix was prepared as described (Reference 32) and a metal bar was placed in the wells. Then, $2\times10^5$ KLN-205 cells/well were seeded and grown overnight to confluency. The cells were treated with 10 μg/ml Mitomycin C (Sigma) for 2 hours after which the cells were washed, and the wound size was measured. For assaying inhibition of cell migration, medium containing 10% FCS was added with or without antibodies and controls (50-100 μg/ml). Cells were allowed to migrate for 46 hours at 37° C. following staining as described above and the wounds were measured and photographed. For quantification of lamellipodia structures at the wound border, five to six fields representing the typical result of KLN-205 cell migration on fibroblast matrix were chosen from two independent studies. Only the first layer of cells at the wound border was counted. The number of cells with lamellipodia/field was compared to the total number of cells/field at the particular wound border.

Analysis of Co/7A1 Expression.

Total RNA was extracted from cultured NIH3T3 cells using RNeasy RNA extraction kit (QIAGEN, Germany), according to the manufacturer's protocol. First strand cDNA was synthesized with reverse transcriptase (Invitrogen, USA) using an oligo-dT primer. PCR reaction was carried out using 35 repeating cycles at 95° C. for 30 seconds, 50° C. for 30 seconds, and 72° C. for 40 seconds with HotStart DNA polymerase (QIAGEN, Germany). Primer sequences for amplification of Col7A1 cDNA were as follows: C7F 5' cagtcaggac-ccaagggtg 3' (SEQ ID NO: 1), C7R 5' tatccgcagcataaccgg 3' (SEQ ID NO: 2), and designed for amplifying the 3' end of mouse Col7A1 mRNA (400 bp). Primers sequences for amplifying part of GAPDH cDNA (347 bp), as positive control, were GAF 5' tcatctccgcccctt 3' (SEQ ID NO: 3), GAR 5' aacacggaaggccatg 3' (SEQ ID NO: 4).

Animal Studies.

All animal studies were performed in accordance with Finnish and Danish laws, and the guidelines for the humane use of animals at Novo Nordisk A/S, Denmark. The studies were approved by Animal Care and Use Committee of the University of Oulu, Finland (064/05) and by The County Administrative Board of Oulu, Finland (OLH-2005-03266/Ym-23).

To analyze targeting of LN-332 antibodies to tumors in vivo, 20 μg IgG/mouse was intravenously injected in PBS into DBA/2 mice harboring KLN-205 tumors (Pab-26 and normal rabbit IgG) or nude mice harboring A431 tumors (mAb-7B2 and normal mouse IgG). For detection of the injected antibody and control IgG, tumor tissues were excised 24 hours after injection. Five μm thick cryosections were fixed with acetone, blocked for nonspecific binding with 1% BSA in PBS, and then studied for presence of the injected antibody using FITC conjugated anti-rabbit IgG or FITC conjugated anti-mouse IgG (Jackson Laboratories).

For immunotherapy studies in a xenograft mouse model, 10-week-old female NMRI nude mice (Taconic) were used. On day 0, human epidermoid carcinoma cells (cell line A431, $2\times10^5$ cells/mouse) were injected s.c. into 30 immunodeficient mice for tumor implantation, after which the mice were divided into three groups (10 mice/group). On day 3 (first dose), and during the treatment period, mice in group 1 received sterile PBS buffer (0.05 ml/10 g). Mice in group 2 got PBS with mAb BM165 (first dose 50 mg/kg in 0.05 ml/10 g, dose during treatment 25 mg/kg in 0.05 ml/10 g). Mice in group 3 got PBS with mAb-7B2 (first dose 50 mg/kg in 0.05 ml/10 g, dose during treatment 25 mg/kg in 0.05 ml/10 g). Therapy injections (PBS with a test item) were given until day 28. Tumor volumes were measured twice weekly, and the study was ended on day 38. The maximum and minimum (length/width) dimensions ($d_1$ and $d_2$) of the tumor were measured and the approximate volume of the tumor was calculated according to the formula $\pi/6 \times d_1^2 \times d_2$ where $d_1 < d_2$.

For immunotherapy studies in a syngeneic mouse model, 8-10-week-old male DBA/2 mice (Taconic) were used. On day 0, murine lung carcinoma cells (cell line KLN-205, $4\times10^5$ cells/mouse) were injected s.c. into 30 mice for tumor implantation, after which the mice were divided randomly into three groups (10 mice/group). On day 7 (first dose), and during the treatment period, mice in group 1 received sterile PBS buffer (0.05 ml/10 g). Mice in group 2 received PBS with mixture of polyclonal antibodies against the short-arms of the γ2 and β3 chains (Pab-1420, Pab-1425 and Pab-226, all doses being 25 mg/kg/antibody in 0.05 ml/10 g). Mice in group 3 received PBS with a mixture of polyclonal antibodies against all chains of LN-332 (Pab-BST, Pab-1425 and Pab-226, all doses being 25 mg/kg/antibody in 0.05 ml/10 g). Therapy injections (PBS with a test item) were given six times. The study was ended on day 28. Tumors were measured twice weekly and tumor volumes were calculated as described previously.

The potential effect of antibodies on the extravasation step of cancer metastasis was studied by intravenous injection of KLN-205 cells. On day 0, $4\times10^5$ cells/mouse were injected i.v. into DBA/2 male mice (8-10-week-old) together with antibodies or the PBS vehicle only. All doses on day 0 and during the treatment were 25 mg/kg/antibody in 0.05 ml/10 g. Mice in group 1 (3 mice/group) received sterile PBS buffer (0.05 ml/10 g). Mice in group 2 (4 mice/group) received PBS with a mixture of polyclonal antibodies against all chains of LN-332 (Pab-BST, Pab-1425 and Pab-226). Mice in group 3 (3 mice/group) received PBS with mixture of polyclonal antibodies against the short-arms of the γ2 and β3 chains (Pab-1425 and Pab-226). Therapy injections (i.p. injections of PBS with a test item) were given three times until day 11 and the study was ended on day 18. The lungs were removed and the lungs γ2 mice/group) representing typical results were subjected to morphological analyses regarding quantity of metastases. Several consecutive 5 μm histological sections (depth of tissue 200-400 nm) were prepared and five sections with regular space and good cross-sections of all lung lobules were scanned for tumor tissue using a Nikon Optishut 2 microscopy connected to a 3CCD color video camera (Sony) and MCIDM4 3.0 Rev. 1.1 software (Imaging Research Inc.). The proportion of tumor tissue per lung sample was calculated as a % of scanned tumor area versus scanned total lung area. The final result was calculated as an average from all 5 lung sections.

To study apoptosis in early primary tumors, human A431 epidermoid carcinoma cells were injected s.c. on day 0 into 18 immunodeficient mice for tumor implantation. On day 3 (first dose) and during the treatment period, mice in group 1 (6 mice) got normal mouse IgG in PBS (Jackson Laboratories, first dose 50 mg/kg in 0.05 ml/10 g, dose during treatment 25 mg/kg in 0.05 ml/10 g). Mice in group 2 (6 mice) got PBS with BM165 (first dose 50 mg/kg in 0.05 ml/10 g, dose during treatment 25 mg/kg in 0.05 ml/10 g). Mice in group 3 (6 mice) got PBS with mAb-7B2 (first dose 50 mg/kg in 0.05 ml/10 g, dose during treatment 25 mg/kg in 0.05 ml/10 g). Therapy injections (i.p. injections of PBS with normal mouse IgG or test items) were given until day 14. Tumor volumes were measured twice weekly. The animals were sacrificed individually depending on the tumor growth on day 7, 10 or 14.

Microarrays.

The effects of antibodies on the expression profiles of A431 cells cultured on fibroblast matrix was studied using DNA microarrays (see Supplementary Materials and Methods). The array data were deposited in the ArrayExpress database. The accession number E-MEXP-1141. Reviewer's account: Username: Reviewer_EMEXP-1141 Password: 1182858855197.

Statistical Analysis.

Data from immunotherapy studies were evaluated by the Mann-Whitney U test and from TUNEL assay by the two-tailed Student t test.

Results

LN-332 mRNA and Protein Expression in Carcinoma Cells.

To identify suitable LN-332 producing cells, we examined expression of the protein in four epithelial cancer cell lines, i.e. mouse KLN-205 squamous cell carcinoma (SCC), human A431, human SCC-25 and human BxPC3 adenocarcinoma. All expressed laminin α3, β3 and γ2 chains, as determined by RT-PCR analysis (FIG. 1A), and Western blotting revealed that all the chains were synthesized with the expected molecular weights (FIG. 1B). The secreted γ2 chain was present in both 155 kDa and processed 105 kDa forms as shown for the mouse KLN-205 cell line.

The LN-332 positive mouse and human tumor cell lines were inoculated into the psoas muscle of DBA/2 mice or the dorsal neck region of nude mice, respectively. All the lines generated LN-332 positive tumors and, additionally, the KLN-205 cells metastasized to the lung. FIG. 1C shows the expression of all LN-332 chains in the human A431 and mouse KLN-205 tumors, the surrounding stroma or muscle tissue being negative, respectively. The expression was strongest at tumor edges, but was also observed more centrally from the tumor front. Lung metastases of KLN-205 primary tumors were LN-332 positive (FIG. 1C). The human SSC-25 tumors revealed similar LN-332 expression (not shown).

LN-332 Antibodies Affect Tumor Cell Adhesion and Migration In Vitro.

Anchorage of epithelial cells is normally mediated through binding of the LN-332 G-domain to integrins on the one hand, and via binding of the short arms of β3 and γ2 chains to matrix molecule like type VII collagen on the other. These binding functions could be interfered with by domain specific antibodies.

Figure 2:
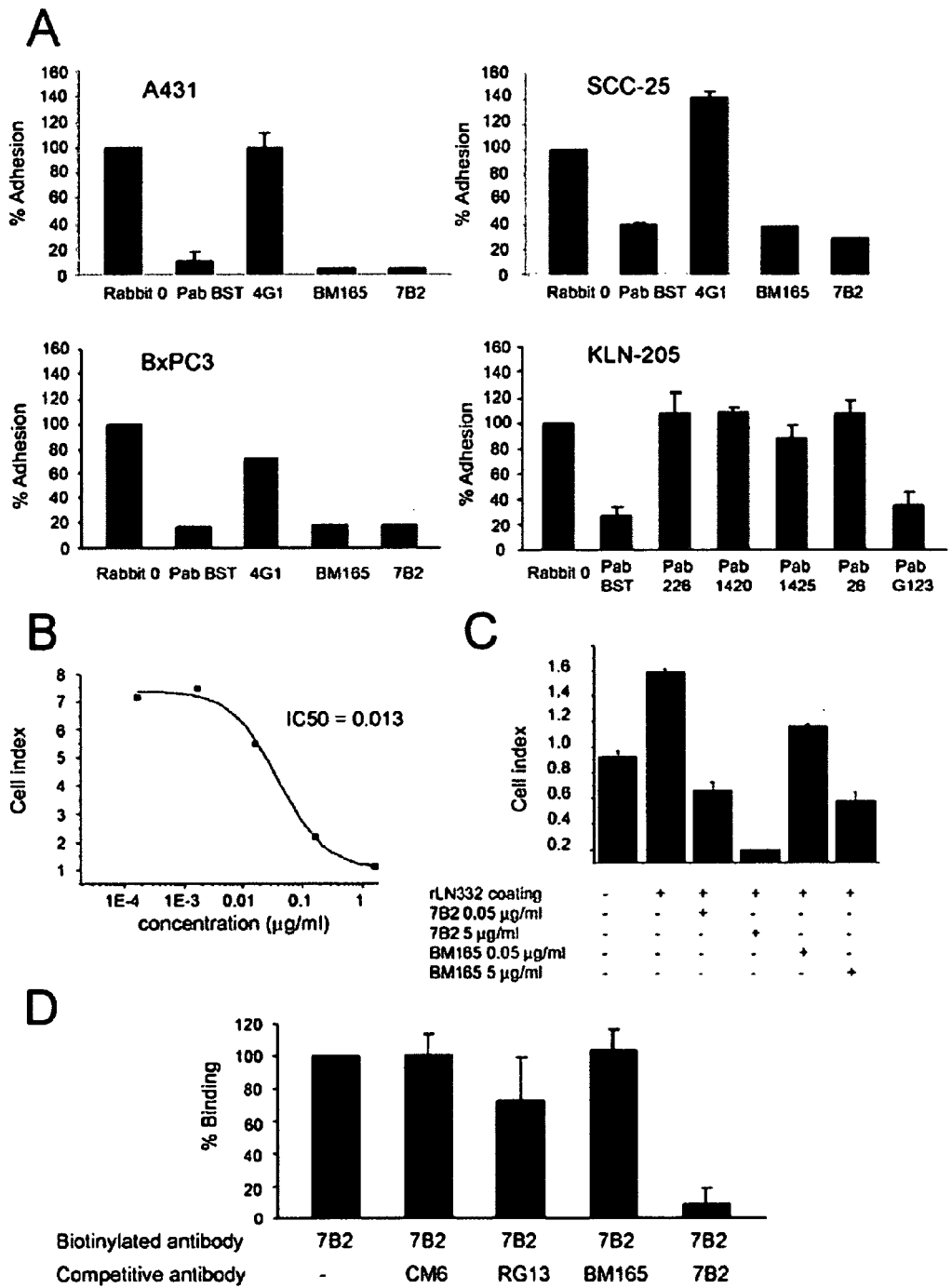
FIG. 2A shows that polyclonal antibody (Pab-BST) raised against trimeric LN-332 and mouse mAbs BM165 and 7B2 directed against the G-domain of the α3 chain significantly inhibited the adhesion of human A431, SCC-25 and BxPC3 carcinoma cells to plastic surface coated with rLN-332. Mouse mAb-4G1 directed against domain III of the short arm of the γ2 chain had no significant inhibitory effect on adhesion of the cells to this surface. Furthermore, Pab-BST and Pab-G123 made against the G1-3 subdomains of the α3 chain inhibited adhesion of the mouse KLN-205 cell line, while Pabs against the short arms of β3 (Pab-226) and γ2 (Pab-1420, Pab-1425, Pab-26) did not affect adhesion of the cells to plastic coated with rLN-332.
FIG. 2B is a graph illustrating the inhibition of cell adhesion by the mAb-7B2 to LN-332-coated surfaces was dose-dependent. The figure shows Cell Index as measured by the RT-CES™ method, at 1 hour after adding 25,000 SCC-25 cells/well (each value is mean of two wells).
FIG. 2C is a comparison of the anti-adhesion effects of anti-α3 mAbs 7B2 and BM165 revealing that mAb-7B2 is twice as potent as BM165 in inhibiting adhesion to LN-322 coated surfaces as shown by the magnitude of Cell Index 1 hour after plating 25,000 A431 cells/well (n=3, mean±SEM).
FIG. 2D illustrates the results of competitive ELISA assays, revealing that mAb-7B2 and BM165 bind different epitopes in the laminin α3 chain G-domain. Biotinylated mAb-7B2 binds effectively to rLN-332 coated plastic (100%). Addition of 100-fold excess of mAb-7B2 inhibits binding of the biotinylated 7B2 antibody, while the same amount of the BM165 or anti-rat α3 antibody CM6 does not inhibit the binding of mAb-7B2 to rLN-332 at all. Another anti-human α3 monoclonal antibody RG13 can only partially inhibit the binding of biotinylated mAb-7B2 to rLN-332.

Pab-BST, generated with the entire human LN-332 molecule as antigen, significantly inhibited adhesion of all cell lines to plastic coated with recombinant human LN-332 (rLN-332) (FIG. 2A). Furthermore, monoclonal antibodies (mAb) BM165 and mAb-7B2, directed against the human G domain revealed similar results. In contrast, antibodies against the short arms of the β3 and γ2 chains did not affect adhesion to rLN-332 in this assay (FIG. 2A). These results agree with the notion that LN-332 is important for adhesion of these tumor cells, and that the major cell and integrin binding site of the protein is located in the G domain of the α3 chain. The inhibitory effect of mAb-7B2 on adhesion to trimeric rLN-332 was dose-dependent (FIG. 2B). The RealTime Cell Electronic Sensing (RT-CES™) technique revealed that mAb-7B2 had almost 50% higher inhibitory effect on cell adhesion than BM165 (FIG. 2C) and the results of the competitive ELISA suggest that mAb-7B2 recognizes, at least partially, different epitopes in the integrin binding domain of the laminin α3 chain (FIG. 2D).

LN-332 antibodies inhibited migration of the cells on uncoated plastic as studied in a two-dimensional wound-healing assay. Thus, mAb-7B2 and BM165 (anti-α3), Pab-BST against raised with rLN-332, but not control IgG (FIGS. 3A and 3B) inhibited the migration of SCC-25, BxPC3 or KLN-205 cells. In contrast, antibodies against domain III (short arm) of the laminin γ2 chain (FIG. 3A) and the short arm of the β3 chain (not shown) did not inhibit migration of the cells in this assay. These results demonstrate that LN-332 is important for migration of the human and mouse carcinoma cells on plastic in the absence of matrix molecules, and that the adhesion of the LN-332 producing cell to the plastic is dependent on the integrin binding G-domain of the α3 chain, but not the short arms of the β3 or γ2 chains that normally connect LN-332 with collagen or other interacting proteins present in the stroma.

Figure 3:
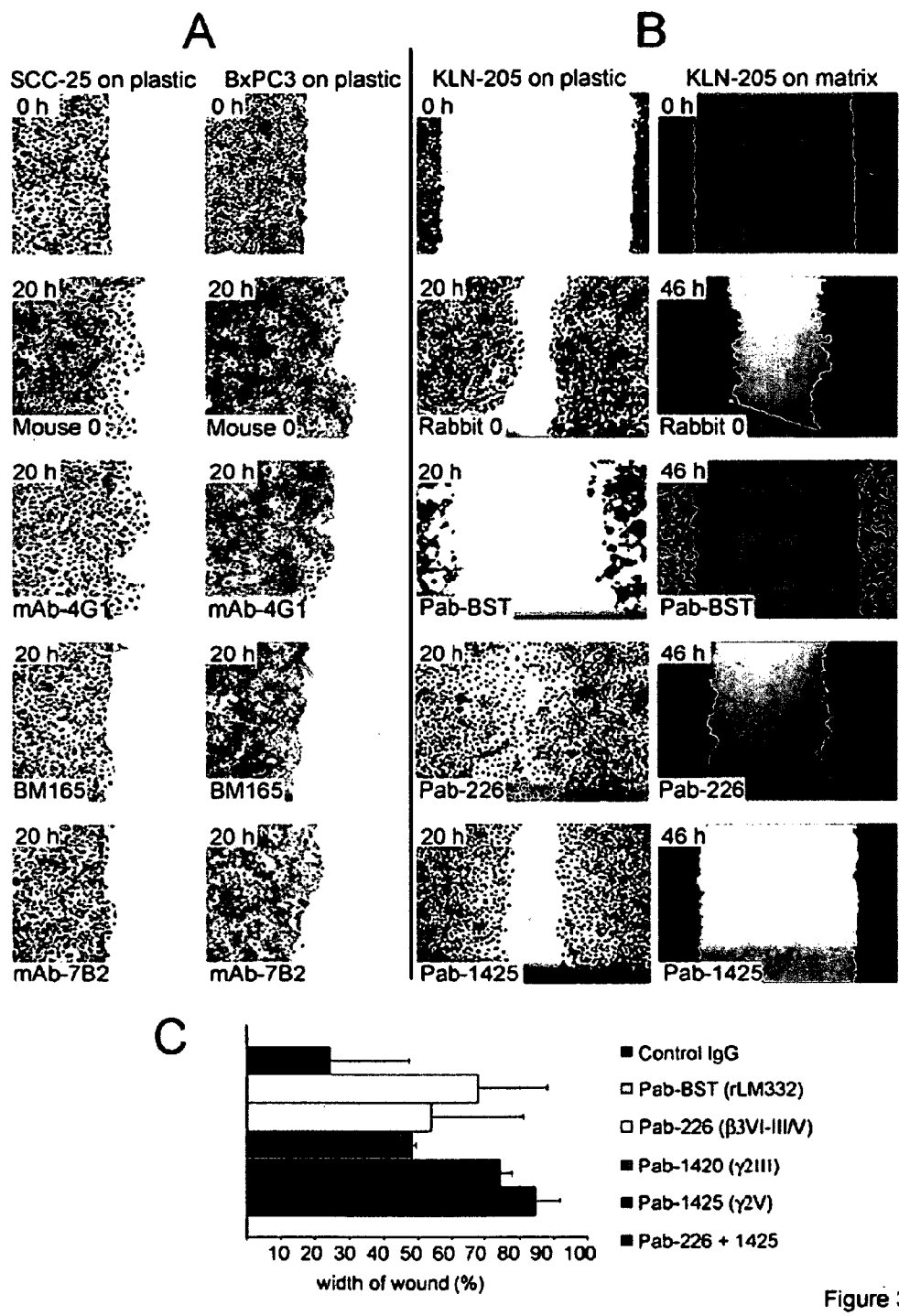
FIG. 3A is pictures of samples with $2 \times 10^5$ SCC-25 or BxPC3 adenocarcinoma cells that were plated on uncoated 24-well plates and grown to confluency after which "wounds" were introduced. Absence of nonimmune IgG (not shown), nonimmune mouse and rabbit IgG or mAb-4G1 directed against the short arm of the γ2 chain did not inhibit migration of either cell type as observed at 24 hours. In contrast polyclonal antibody Pab-BST made against whole trimeric LN-332 and mAbs BM165 and 7B2 that target the G-domain of the α3 chain effectively inhibited migration of the cells.
FIG. 3B is pictures of samples with $2 \times 10^5$ mouse KLN-205 cells that were plated on uncoated plastic or a fibroblast-derived matrix containing type VII collagen. Non-immune rabbit IgG or Pab-226 (β3 chain) or Pab-1425 (γ2 chain) did not affect migration on uncoated plastic. However, Pab-BST that reacts with mouse LN-332 effectively inhibited migration and also caused some dissociation of the cells. However, if the cells were grown on fibroblast-derived matrix, antibodies against the short arms of β3 and γ2 all inhibited migration, although the anti-β3 antibody did not inhibit migration completely. Non-immune rabbit serum had no effects on migration. In all migration experiments, Mitomycin was added to prevent cell proliferation and the cell position was documented at 0 and 24 hours as described in Materials and Methods below.
FIG. 3C is a graph summarizing the effects on different LN-332 antibodies on migration of mouse KLN-2 cells on fibroblast-derived matrix.
Figure 10:
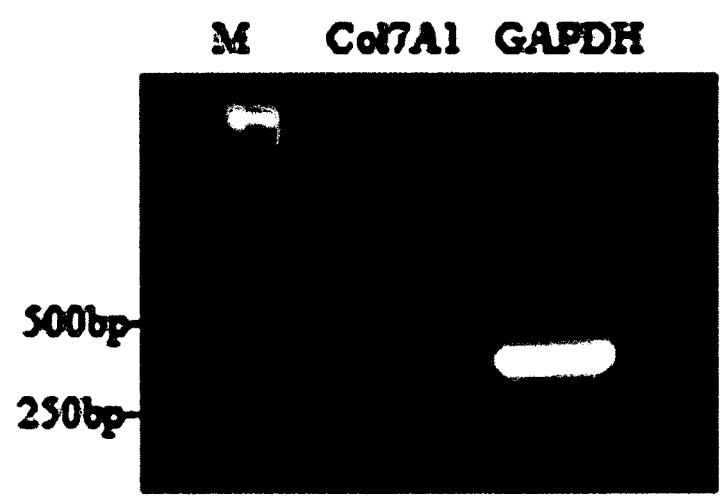
FIG. 10 shows the expression of the type VII collagen al chain by mouse NIH-3T3 fibroblasts. RT-PCR analysis reveals expression of type VII collagen al chain (Col7A1) in mouse NIH-3T3 fibroblasts used in this study. Expression of the housekeeping GAPDH gene is shown as a control.

Epithelial cells are normally anchored in vivo to stroma molecules, such as type VII collagen, through the short arms of LN-332, so we repeated the migration studies of the tumor cells on a fibroblast-derived matrix containing type VII collagen. The mouse fibroblast cell line NIH-3T3 used for the production of matrix was demonstrated to express type VII collagen using RT-PCR assay (Materials and Methods, FIG. 10). Interestingly, the migration of murine KLN-205 cells grown on such a matrix was strongly inhibited by antibodies against the short arms of both β3 and γ2 (Pab-226, P-1420, Pab-1425), and an antibody against whole trimeric LN-332 (Pab-BST) (FIG. 3B). This demonstrates that domains III and V of the γ2 chain and the short arm of the β3 chain are important for linking LN-332 to the matrix during migration. We also tested effects of the antibodies against the α3, β3 and γ2 chains on migration of human SCC-25 carcinoma cells on the fibroblast matrix and they yielded similar inhibitory effects (data not shown). The overall effects of different antibodies on migration are depicted in FIG. 3C.

Figure 4:
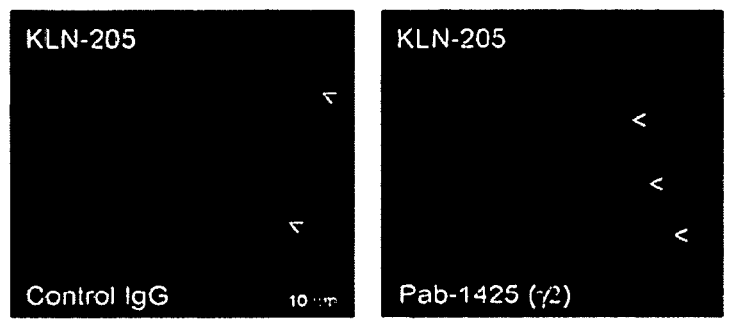
FIG. 4A is two pictures showing the effects of antibodies against the γ2 chain on mouse KLN-205 SCC cell migration on fibroblast-derived matrix, along with a control. In the presence of non-immune serum, the cells generate broad lamellipodia in the direction of migration, but addition of the Pab-1425 antibody targeting domain V of the γ2 chain inhibits the lamellipodia formation completely. For detection of changes of phenotype of KLN-205 cells migrating on fibroblast derived matrix, actin fibers were stained with 0.004 units/ml rhodamine-phalloidin (Molecular Probes, Invitrogen, R-415) and cell nuclei were stained with Hoechst stain. Arrows point to the periphery of lamellipodia positive or negative cells. Magnification 400×.
FIG. 4B is a graph summarizing the effects of antibodies against the γ2 chain on the shape of mouse KLN-205 SCC cells.
Figure 4:
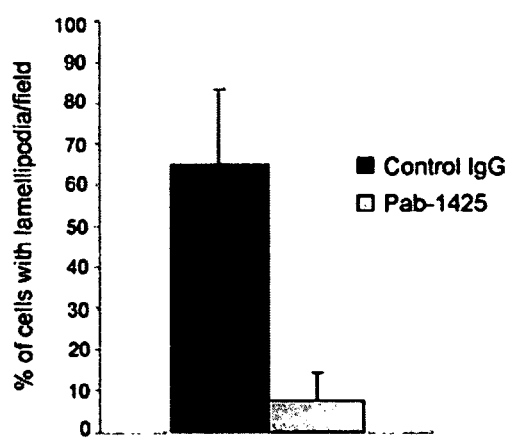

LN-332 antibodies generated different cellular phenotypes in cells grown on the fibroblast-derived matrix. Thus, antibodies against the integrin binding G-domain caused many of the cells to round up and detach, while the antibodies against the short arms of β3 and γ2 (Pab-226 and Pab-1425) inhibited the formation of lamellipodia that are seen in a migratory cell (FIG. 4A). This shows that the migratory cell uses the short arms to bind to stroma molecules during migration. Cells with lamellipodia were quantified and the number of cells with lamellipodia was compared to the total number of cells at the wound border. About 65% of cells treated with control IgG had migratory phenotype with lamellipodia structures at the wound border whereas lamellipodia was seen in only 7.7% of cells treated with e.g. Pab-1425 (FIG. 4B).

LN-332 Antibodies Target Carcinomas In Vivo.

Figure 5:
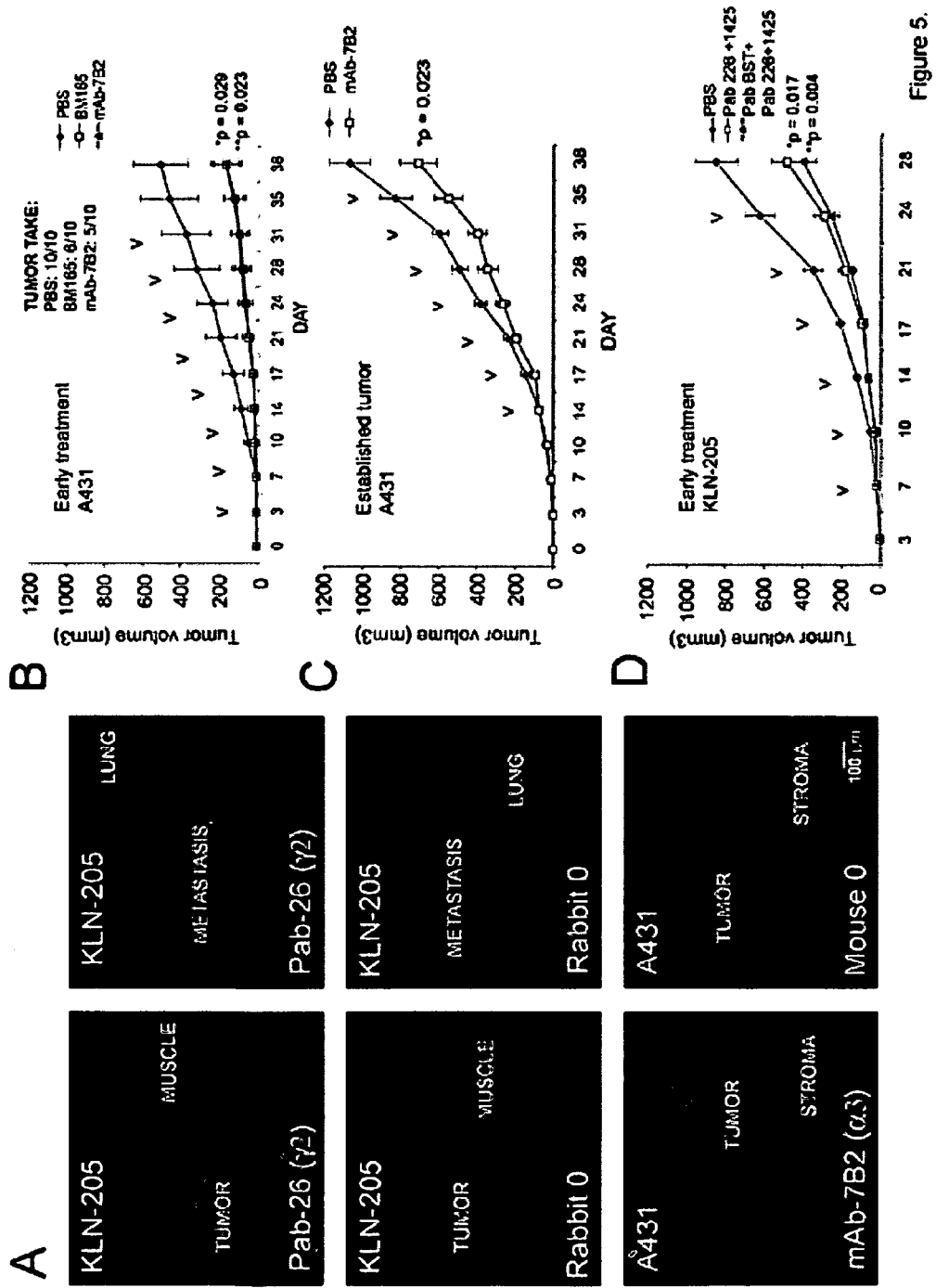
FIG. 5A is a set of pictures showing antibodies against whole LN-332 or individual laminin chains that were injected intravenously into tumor harboring mice after which the tumors were excised and tissue/tumor sections were stained with a labeled secondary antibody. mAb-7B2 against the α3 chain targets A431 tumors in nude mice, while non-immune mouse serum does not target the tumor cells in vivo. Polyclonal rabbit anti-human laminin γ2 chain antibodies (Pab-26) effectively target a murine KLN-205 primary tumor growing in the psoas muscle, or its lung metastasis. Normal rabbit IgG does not target to tumors or other mouse tissues. Magnification 200×.
FIG. 5B is a graph illustrating the results of an experiment where $2 \times 10^5$ cells were injected s.c. in the dorsal neck region of 30 nude mice. From day 3, the mice were treated twice a week with BM-165, mAb-7B2 or PBS until day 24, and then observed further to day 38 when they were sacrificed and analyzed. The tumor growth was statistically significantly decreased following injections of the anti-α3 chain antibodies. The tumor sizes are presented as $mm^3$, the bars representing +/−SEM. The arrows depict times of antibody injections.
FIG. 5C shows the results of a study with established tumors, where the treatment of antibodies was initiated first at day 14 when the tumor volumes were 50-100 $mm^3$ and then treated with mAb 7B2 or PBS. Otherwise, the procedure was as in FIG. 5B.
FIG. 5D demonstrates the results of a study with established murine tumors, where $4 \times 10^5$ KLN-205 cells/mouse were injected s.c. into 30 mice for tumor implantation. The treatment of antibodies or antibody mixtures (Pab-BST, Pab-1425 and Pab-226) was initiated at day 7 when the tumor volumes were about 20 $mm^3$ and continued until day 24. The study was finished at day 28.

Anti-LN-332 antibodies injected intravenously into mice harboring LN-332 producing tumors targeted to the tumors and their metastases. We first injected α3 and γ2 chain antibodies into nude mice harboring subcutaneous human A431 tumors. The α3 mAb-7B2 antibody effectively targeted the tumors 24 hours after injection (FIG. 5A), the staining being mainly seen in the periphery close to the stromal component. Antibodies to β3 and γ2 showed similar staining of the tumor cells (not shown). Additionally, some discontinuous staining could be detected surrounding tumor cell colonies and around some single cells. Normal mouse IgG gave no positive staining (FIG. 5A). The β3 and γ2 chains are only present in the LN-332 isoform, but the α3 chain is also present in LN-311 (previously laminin-6) and LN-321 (previously laminin-7) isoforms (Reference 1). The mAb-7B2 gave only weakly positive signal in blood vessels indicating that it might react with those laminins also (data not shown). Since neither mAb-7B2 nor BM165 really cross-react with murine LN-332, the potential in vivo homing of these antibodies to normal epithelia and blood vessels remains to be confirmed with anti-mouse α3 chain antibodies in syngeneic mouse models.

We then injected purified polyclonal rabbit IgG directed against the laminin γ2 chain or normal IgG into mice harboring murine KLN-205 primary tumors and lung metastases. The mice were sacrificed 6, 24, 48 or 72 hours after injection and frozen sections were examined for rabbit IgG with a FITC-labeled anti-rabbit secondary antibody. Six hours after injection, the anti-γ2 antibodies had effectively targeted the primary tumor and its lung metastases, as opposed to control IgG (FIG. 5A). Staining was seen throughout the KLN-205 tumor tissue, the reaction being strongest at the muscle-tumor interface. Additionally, some discontinuous staining could be detected surrounding tumor cell colonies and around some individual cells. The specific location of the anti-γ2 chain antibody could be seen already 6 hours after injection, and it was still detectable for at least 7 days after injection (data not shown). Tumors and other tissues were negative with the labeled anti-rabbit second antibody following injections of normal rabbit IgG (not shown).

The polyclonal LN-332 antibodies did show some targeting to normal epithelial BMs such as in the skin and intestine, but the staining was not as intense as in the tumors. We never noticed any signs of skin blisters or abnormalities in the intestinal epithelia that are seen in patients with junctional epidermolysis bullosa or LN-332 knockout mice after antibody treatment for up to four weeks.

Anti-Laminin-Antibodies Inhibit Growth of Human A431 and Murine KLN-205 SCC In Vivo.

We explored if LN-332 antibodies could possibly affect growth and spread of tumor cells in vivo. Four independent studies were performed using highly LN-332 positive human A431 tumors in nude mice (xenograft model) and murine KLN-205 tumors in DBA/2 mice (syngeneic metastasis model) as models. Both BM165 and mAb-7B2 caused significant inhibition of primary tumor growth in A431 xenograft model, the overall inhibition being up to 68% (FIG. 5B). The tumor take of treated tumors was lower (55%) in study 1 (FIG. 5B) than in study 2 (100%) (data not shown), suggesting the anti-tumor effect was partially due to reduced tumor establishment for the antibody treated mice. The inhibition of tumor growth with BM165 was 68% ($p=0.029$) in study 1 and 48% ($p=0.113$) in study 2, and the inhibition with mAb-7B2 treatment was, respectively, 68% ($p=0.023$) and 51% ($p=0.028$).

In the third study, the treatment with the mAb-7B2 anti-α3 chain antibody was started first at day 14 when the tumors were established (50-100 mm$^3$). There was still a significant inhibitory effect on tumor growth, although it was only 34% ($p<0.001$) (FIG. 5C).

In the fourth study with the murine KLN-205 tumor model, the treatment with polyclonal antibodies against all three LN-332 chains or only against the β3 and γ2 short-arms was started 7 days after tumor inoculation when tumor take was 100% and tumor volumes were about 20 mm$^3$. The inhibition of tumor growth with the short arm antibodies was about 43% and with the antibody mixture against all LN-332 chains was about 53% (FIG. 5D).

To study the potential activation of the normal immunological system, blood samples were analyzed from A431 in vivo studies and from normal nude mice treated with isotype-matched anti-LN-332 monoclonal antibody that also localizes to tumors in vivo. However, no signs of neutralizing antibodies were detected (data not shown). In addition, only a minor inhibitory effect on tumor growth was detected in mice harboring murine KLN-205 tumors when treated with isotype-matched polyclonal antibody Pab-26 against the γ2 chain domain III (data not shown) that has also been shown to localize in tumors in vivo. Thus, the major mechanism of tumor growth inhibition is most likely not a consequence of e.g. activation of complement proteins.

Figure 6:
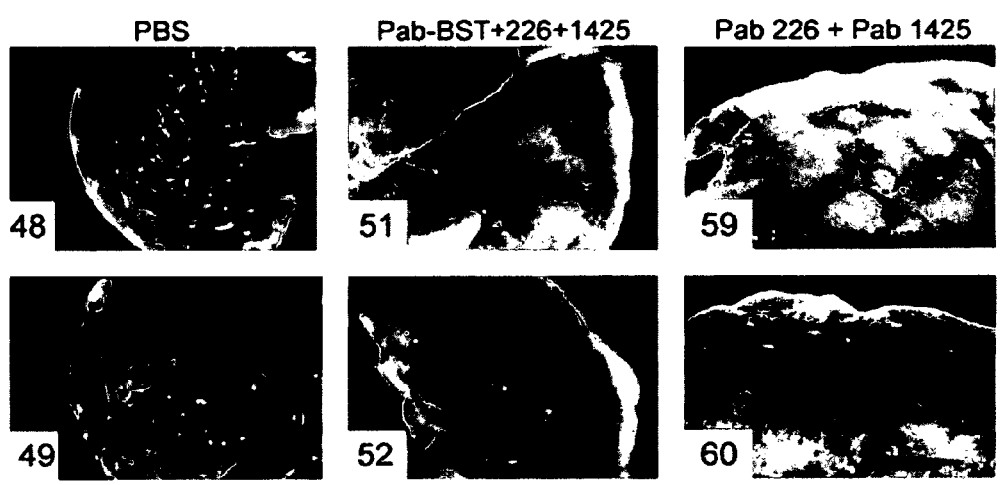
FIG. 6A is six pictures showing the effect of LN-332 antibodies on metastasis of invasive carcinoma cells in mice. KLN-205 carcinoma cells were injected intravenously with PBS only or with antibodies against whole LN-332 or short-arms of β3 and γ2 chains. After the treatment period, the lungs were removed and subjected to analyses of metastases. Antibodies against both whole LN-332 (mice 51 & 52) and short-arms of β3 and γ2 chains (mice 59 & 60) inhibit effectively the formation of metastases in lungs compared to mice treated with vehicle only (mice 48 & 49).
FIG. 6B shows histological sections from the lung lobules of FIG. 6A. HE counterstain.
FIG. 6C is a morphological quantification of tumor tissue per lung sample.
Figure 6:
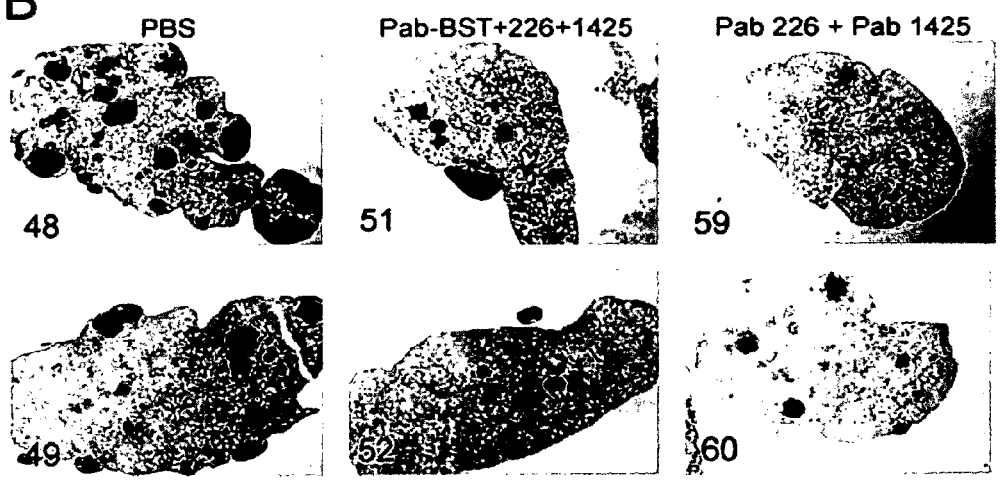
Figure 6:
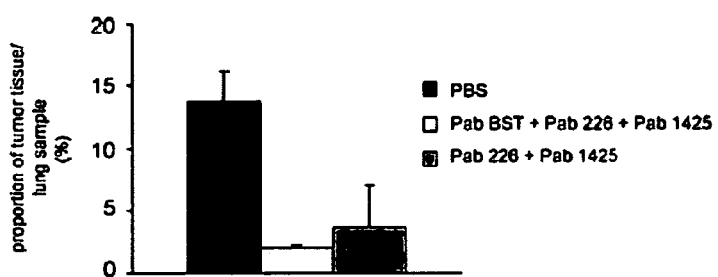

An important question was whether anti-LN-332 antibodies interfering with migration via binding to the matrix binding short arms of the β3 and γ2 chains would affect the formation of metastasis in vivo. Importantly, this was shown to be the case. Thus, the polyclonal antibody mixture against all three LN-332 chains on the one hand, and antibodies against the β3 and γ2 short-arms on the other, reduced the number of pulmonary metastases by about 70-85% following i.v. injection of the murine KLN205 cells (FIG. 6).

Figure 7:
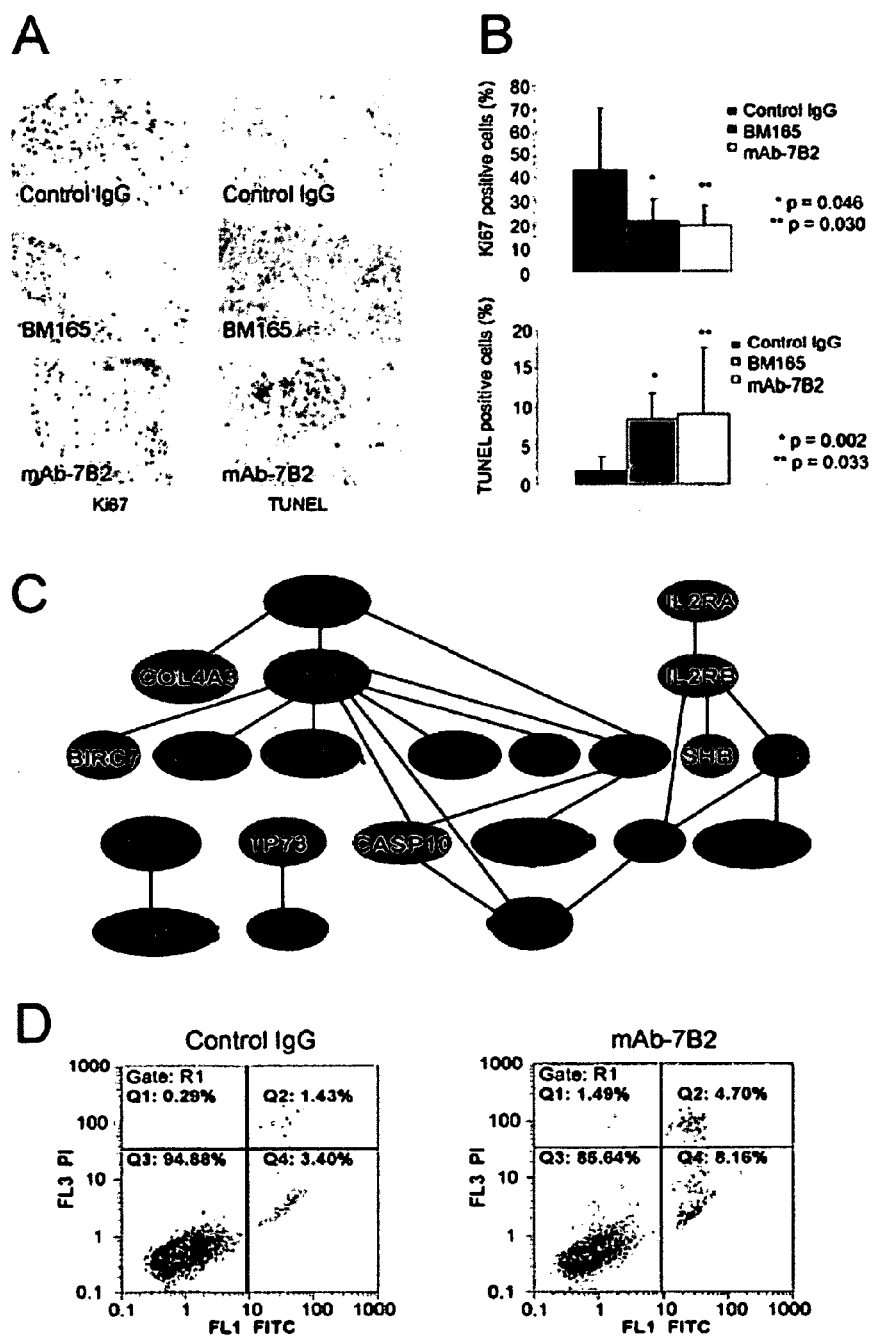
FIG. 7A is a staining of early primary tumors with polyclonal anti-Ki67 and TUNEL staining showed a significant reduction in the number of proliferating cells and increase in tumor cell apoptosis on day 7 after treatment with BM165 or mAb-7B2.
FIG. 7B is statistical analyses of anti-Ki67 and TUNEL stainings from untreated and treated tissue samples as exemplified in FIG. 7A.
FIG. 7C shows the protein-protein interaction network of some differentially expressed genes related to apoptosis. The literature validated protein interaction data was extracted from the Human Protein Reference Database (www.hprd.org). A number of genes related to the apoptosis were upregulated (red) in A431 cells plated on fibroblast-derived matrix and treated with anti-LN-332 antibodies.
FIG. 7D shows the number of apoptotic cells was 2.4 times higher in cells treated with MAb-7B2 than in cells subjected to normal mouse IgG as analyzed by flow cytometry following labeling of the cells with Annexin V.

To get insight into the mechanisms of tumor growth inhibition, we examined the A431 tumors for levels of proliferation and apoptosis with or without antibody treatment. Antibody injections (PBS with normal mouse IgG, BM165 or mAb-7B2) were given from day 3 until day 14 (3 times). The animals were sacrificed individually depending on the tumor growth on day 7, 10 and 14. Staining of early primary tumors with polyclonal anti-Ki67 showed a significant reduction in the number of proliferating cells in early tumors on day 7 after treatment with BM165 or mAb-7B2 (FIGS. 7A and 7B). TUNEL staining of 7-day-old tumors indicated an increase in tumor cell apoptosis (FIG. 7A). The apoptotic index of tumors from mice treated with BM165 and mAb-7B2 (8.48%±3.25% for BM165, $P=0.002$ and 8.18%±8.46% for mAb-7B2, $P=0.033$) was significantly higher on day 7 than that of mice treated with mouse normal IgG (1.82%±1.28%) that was used as a control (FIG. 7B). Similar results were obtained also for day 14, but not in the end of the in vivo study on day 38 (data not shown).

To find out about the molecular mechanisms of tumor growth inhibition caused by the LN-332 antibodies, human A431 cells were plated on fibroblast-derived matrix for five hours, before adding a mixture of antibodies against all three LN-332 chains, and the incubation was continued for 16 hours. About 30% of the cells rounded up, some of them becoming detached, while the control cells remained attached. Cells from antibody treated and controls were subjected to global transcriptome analysis using Affymetrix Human Genome U133 Plus 2.0 Arrays. The results revealed that 2,139 genes were differentially expressed at least 1.5-fold change at 5% individual significance level. A total of 1,291 genes were upregulated at 1.5-fold or more in antibody treated cells, and 848 genes were downregulated 1.5-fold or more.

Interestingly, a number of genes of the apoptosis pathway were upregulated (see FIG. 7C and Supplementary Table 1). For example, caspase 3 was upregulated about 10-fold, DNase 16-fold, caspase 4 3-fold and death associated protein 3 2-fold.

The proportion of apoptotic cells after anti-LN-332 treatment was analyzed by flow cytometry, following labeling of the cells with Annexin V. As shown in FIG. 7D, the number of apoptotic cells was 2.4 times higher in cells treated with mAb-7B2 than in cells subjected to normal human IgG. There are other pathways or biological processes that are significantly altered, such as the regulation of cellular process, integrin-mediated signaling pathway, cell adhesion, regulation of cell growth, etc. It could be a secondary effect for many of these pathways to be altered. Therefore, we chose to focus on the apoptosis pathway, which is directly linked to the observed phenotype. Thus, all the interactions are literature validated protein-protein interactions taken from the Human Protein Reference Database (www.hprd.org) (33-35).

Discussion

LN-332 is an epithelium specific adhesion and migration related protein that is highly expressed in most epithelial tumors, such as squamous cell carcinomas of skin, oral cavity, gastrointestinal tract, and colon and cervix cancers (References 15, 16, 19, and 36-40). The present application showed that domain specific antibodies can significantly affect specific functions of LN-332 and the behavior of LN-332 positive tumor cells in vitro and in vivo. First, β3 and γ2 chain specific antibodies were, for the first time, shown to inhibit LN-332 mediated tumor cell migration on stroma matrix, suggesting that the stroma-binding function of LN-332 is important for migration through the matrix. Second, blocking of the integrin binding site of the α3 chain also inhibited adhesion and migration of LN-332 positive tumor cell lines. Third, these antibodies by detaching the cells in vitro induced apoptosis. Fourth, and importantly, the antibodies effectively targeted LN-332 positive human tumors mice in vivo. Fifth, treatment of mice harboring human A431 and murine KLN-205 carcinomas with LN332 antibodies resulted in significant decrease in tumor growth. Sixth, the formation of lung metastasis by intravenously administered KLN-205 tumor cells was significantly reduced by treatment with antibodies against LN-332. The results suggest that such antibodies may have a potential as therapeutics that can both inhibit tumor growth and the process of tumor spread.

Inhibition of Adhesion and Migration.

Antibody-mediated neutralization LN-332 function of tumor cells in vivo requires specific blocking of the cell binding domain on the one hand, and the matrix binding domains on the other, and that the antibodies do not cause dysfunction and complications of normal epithelia such as skin blisters. This study demonstrated that targeting of the integrin-binding G-domain effectively inhibited adhesion of LN-332 positive cells to plastic coated with rLN-332, and migration on plastic or fibroblast-derived matrix. Previous studies have shown that epithelial and carcinoma cells bind to LN-332 through integrins α3131 and α6β4 (Reference 11). In stationary adhesion, α6β4 is the main integrin (Reference 11), but during migration, it is primarily α361 (References 41 and 42). Although antibodies against both integrins inhibit binding to LN-332, specific blocking of the LN-332 binding to integrins is probably more effectively achieved with antibodies against the LN-332 G-domain, as antibodies against the integrins affect the binding of those receptors to a number of other proteins in various cells types and tissues.

While antibodies against the short arms of LN-332 β3 and γ2 chains did not affect binding or migration on LN-332 coated plastic, they did block migration on the fibroblast derived matrix. A reasonable explanation is that in tissues LN-332 interacts through its short arms with type VII collagen, and that this interaction is utilized for migration within the stroma. This type of laminin-stroma interaction in anchoring filaments is unique for LN-332, the only laminin type containing the β3 and γ2 chains. No other laminins knowingly bind to type VII collagen. LN-332 has been shown to bind to type VII collagen through its short arms (Reference 14), but it has not been clarified if both chains participate in this interaction. The present results strongly suggest that both chains are involved, as antibodies against the entire short arm of β3, or against domains III or V of γ2 individually affected migration on the stroma matrix. Further evidence for the role of the γ2 chain in the binding to stroma proteins is that an in-frame deletion of a segment of domains III and IV (Pab-1420 antigen) causes lethal junctional epidermolysis bullosa (Reference 7). In addition to type VII collagen, the short arm of γ2 has been suggested to bind fibulin-2, α2β1 integrin, heparin/heparin sulfate or syndecan-1 at least in vitro (References 43-46), but if those results are relevant in vivo remains to be shown.

Interestingly, the antibodies against the LN-332 short arms inhibited the lamellipodia formation normally associated with migrating epithelial cells. Lamellipodia formation is initiated by polarized polymerization of actin and generation of initial protrusions (References 47 and 48) This does not require extracellular matrix interactions in vitro, but the protrusions are never as large as lamellipodia formed when cells are plated on adhesive substrates (Reference 49). The role of the LN-332/type VII collagen interaction in formation of lamellipodia and migration has not been elucidated. However, it has been shown that during transition from a stable adhesive phenotype to a migratory one, the cell forms lamellipodia with α3β1 integrin expressed at the leading edge (References 41, 42, and 50). Such migration, when occurring by LN-332 producing cells cultured on denatured rat tail collagen, was α3β1 and Rac1 activation dependent, and α3 integrin deficient keratinocytes did not form lamellipodia under these conditions (Reference 42). Antibodies against α6β4 and α3β1 integrins block the interaction with LN-332 and, thus, this migration. The present results showed that not only does the blocking of the G-domain block the migration on a stromal matrix, but that blocking of short arm function also inhibits lamellipodia formation and migration. This suggests that the forming lamellipodia use the combined interaction of integrin, LN-332 and type VII collagen and possibly other stromal proteins during the migratory process. This can correspond to the process normally occurring during epithelium and carcinoma cell migration in vivo.

Conclusively, our results showed that the LN-332 molecule uses the short arms of both β3 and γ2 to bind to stromal proteins during migration, in addition to the role of the G-domain for cellular binding, and that these functions can be blocked, at least in vitro with domain specific antibodies.

LN-332 Antibodies Target Carcinoma In Vivo and Induce Apoptosis.

Several studies have previously shown that cells at the invasive front of carcinomas are often positive for LN-332 expression (References 15, 16, 19, 36, and 37). Here, we showed that antibodies to different LN-332 domains readily target such carcinomas in vivo. Furthermore, we showed that mAbs BM-165 and 7B2, which are directed against the integrin-binding domain on the α3 chain of the protein, significantly inhibited growth of human A431 SCC in nude mice when injected 3 days after inoculation of the tumor cells. In addition, the polyclonal antibodies against the short-arms of β3 and γ2 chains were able to inhibit tumor growth in KLN-205 mice when treatment has been started early.

As the A431 tumor grows in vivo, its central parts stop proliferating, apoptosis is increased and the center becomes necrotic. The most actively proliferating cells are located at the periphery of the tumor nests as we have observed with proliferation markers (data not shown). Recently it has been reported by Atsumi that peripheral cells of A431 tumor nests are enriched by cancer-initiating cells (cancer stem cells) (Reference 58). Since LN-332 expression was predominant at the invading periphery of A431 tumor nests and since mAb-7B2 also targets the periphery of tumor nests, our antibodies may actually target these cancer-initiating cells.

The present and previous studies have demonstrated the importance of LN-332 for tumorigenesis and invasion, and this makes LN-332 an interesting target for cancer therapy. Dajee et al. (Reference 25) showed that SCC cells overexpressing ras-IκBα exhibit high expression of LN-332 and α6β4 integrins, and that the growth of such tumors can be inhibited completely by mAb BM165 or antibodies against α6β4 integrin, and that LN-332 or α6β4 negative cells overexpressing ras-IκBα did not form tumors. However, we never accomplished more than 68% inhibition of tumor growth with mAb BM165 in the present study. The importance of the LN-332-stroma interaction was also emphasized in a study showing that keratinocytes from epidermolysis bullosa patients with non-functional type VII collagen gene do not form tumors, while normal keratinocytes overexpressing ras-IκBα were tumorigenic (Reference 51). Furthermore, it has been shown that epidermal tumorigenesis and PI3K pathway activation are associated with LN-332 and type VII collagen interactions (Reference 52). The interaction of the β3 chain with type VII collagen has been suggested to be essential for SCC tumorigenesis, increased tumor invasion and protection from apoptosis.

LN-332 has also been shown to affect the malignant potential of tumor cells and enhance tumorigenicity of human fibrosarcoma cells HT1080 in nude mice. HT1080 cells transfectants expressing LN-332 grew faster and formed larger tumors than the control cells (Reference 24). However, contradictory results also exist (Reference 53). Thus, suppression of LN-332 expression in non-invasive oral squamous carcinoma cells JHU-022-SCC enhanced in vivo tumorigenicity and invasion.

The mechanisms of tumor growth inhibition are not known, but it is likely that dissociation of the tumor cells from the surrounding stroma causes anoikis (Reference 54) and subsequent apoptosis. Our expression analyses of SCC cells grown on stromal matrix and treated with a combination of antibodies against the integrin-binding domain, as well as against the short arms of LN-332 suggested that this is likely to be the case. Migration of the cells was clearly inhibited and the cells frequently rounded up and detached from the substrate. Compared with untreated cells, there was significant upregulation of several components of the caspase cascade, such as caspase 3, caspase 8, DNase I and programmed death protein 3 in treated cells. These findings are typical for anoikis, which has been defined as apoptosis induced by inadequate or inappropriate cell-matrix interaction (Reference 54). Loss of integrin-mediated cell adhesion somehow evokes apoptotic pathways, but stable binding of cells to LN-332 induces anti-apoptotic signals to the cell through the actions of focal adhesion kinase, PI 3 kinase and MAP pathways (References 54, 55). It has been reported that transfection of metastatic lung carcinoma cells with LN-332 protects against anoikis (Reference 56). Although dissociation of LN-332 from the integrin must be the primary trigger of apoptosis, the cellular dissociation is more complete if the LN-332 is also detached from type VII collagen and potentially from some other stromal proteins with the antibodies against the short arms.

LN-332 Antibodies Reduce Metastasis of Invasive Carcinoma Cells.

An important finding of this study was that LN-332 antibodies significantly reduce the number of metastatic foci of the murine KLN-205 cells that had been administered intravenously. The process of carcinoma cell metastasis is a complex process involving numerous individual molecular events such as dissociation of the transformed epithelial cell from its underlying basement membrane, degradation of the surrounding extracellular matrix by a complex process of proteolysis and migration of the tumor cell (Reference 57). As described above, the migration of a LN-332 positive tumor cell at the invasive tumor front involves among other events binding of the tumor cell to matrix molecules such as type VII collagen. This study showed that antibodies targeting the matrix binding region of LN-332 can inhibit this function and thus contribute to the reduction of metastasis.

The present study has provided new insight into the role of LN-332 for adhesion and migration and how important the cellular interaction of this protein is for LN-332 dependent cell survival. It is evident that dissociation of this protein from the carcinoma cells induces apoptotic pathways and tumor cell death even in vivo. It is similarly apparent from the present results that targeting of the short arms of LN-332 may inhibit the actual in vivo migration mechanism via binding to type VII collagen and possibly some other stromal components. At the present, no clinically used drugs target the migration mechanisms of tumor cells. In this investigation, polyclonal antibodies against the mouse LN-332 were used.

Supplementary Materials and Methods

Proteins and Antibodies.

Recombinant LN-332 (rLN-332) was prepared as described in U.S. Pat. No. 6,703,363. Recombinant laminin α3 G-domain fragments G12 (rG12) and G123 (rG123) were produced in FS 293 cells (Invitrogen) by transient transfection of the expression vectors, pRCx3 α3G12 and pRCx3 α3G123. These vectors contained the completed sequences, verified by DNA sequencing, of G12 and G123 domains, respectively.

The coding sequences for α3G12 and α3G123 were PCR-amplified using as template the expression vector for the LN-332 α3 chain, pZeo alpha3 (U.S. Pat. No. 6,703,363), and the following primers:

```
g123Fwd,
GCTAGCCCTGGAAGATTTGAA         (SEQ ID NO: 5)
and
```

-continued

```
g123Rev,
ATCGATCAGGGAAGTGGTGAGCAAG      (SEQ ID NO: 6)
for α3G123 and g123 fwd and g12 rev,
ATCGATCACACAAGCTTCCAGTCTTCC    (SEQ ID NO: 7)
for α3G12.
```

Recombinant laminin β3 short-arm 65 kD fragment (rβ3-65 kD) was purified from a stable HEK 293 cell line transfected with LN-332 β3 expression vector, pRcX3 beta3 (U.S. Pat. No. 6,703,363).

All these LN-332 fragments were expressed carrying a Flag sequence (Sigma) at the amino terminus end, enabling a single-step affinity chromatography purification procedure for these recombinant proteins.

For the production of polyclonal antibodies against murine laminin γ2 chain a part of domain III of the murine γ2 chain was expressed as a GST fusion protein (Pab1420). A DNA fragment encompassing nucleotides 1312-1888 (Genebank NM_008485) was generated by PCR and subcloned into the EcoRI site of the pGEX-I\T expression vector (GE Healthcare). The sequence of the PCR product was confirmed by DNA sequencing. The fusion protein was produced in E. coli BL21 cells (Promega) upon induction with isopropyl-β-D-thiogalactoside and purified on a glutathione-Sepharose 4B column as recommended by the manufacturer (GE Healthcare). For the production of polyclonal antibodies a part of domain V of the murine γ2 chain was expressed as a GST fusion protein (Pab-1425). A DNA fragment encompassing nucleotides 66-585 (Genebank NM-008485) was generated by PCR and subcloned into the EcoRI site of the pGEX-I\T expression vector (GE Healthcare). The sequence of the PCR product was confirmed by DNA sequencing. The fusion protein was produced in E. coli BL21 cells (Promega) upon induction with isopropyl-β-D-thiogalactoside and purified on a glutathione-Sepharose 4B column as recommended by the manufacturer (GE Healthcare). Both Pab-1420 and Pab-1425 were raised in rabbits and characterized using ELISA, immunohistochemistry and western analysis.

Real-time PCR. Total RNA from SCC-25, A431, BxPC3 and KLN-205 cells was reverse transcribed to cDNA by random hexamer primers with RevertAid™ first strand cDNA synthesis kit (Fermentas Life Sciences). Real-time PCR was performed in ABI 7500 Real Time PCR System (Applied Biosystems) using TaqMan probe-based chemistry. Sequences for primers and probes were as follows: laminin-332 5'-GGCTACTTCGGGGACCATT-3' (SEQ ID NO: 8), 5'-TGCAAACACAGGTGCCATCAC-3' (SEQ ID NO: 9), and 5'-CAGACAAGTGTCGAGCTTGCAACT-3' (SEQ ID NO: 10) (probe); type VII collagen 5'-GTGGCTGACCAT-GTCTTCCT-3' (SEQ ID NO: 11), 5'-CCACCAGGTC-CTGGGACTT-3' (SEQ ID NO: 12), and 5'-TGTCCCCAAG-GTCTGCATCCTGA-3' (SEQ ID NO: 13) (probe). The relative quantification of each target gene expression was performed with comparative cycle threshold ($C_T$) method. S18 mRNA was used as an endogenous control.

Western Blotting.

A431, SCC-25 and BxPC3 cells from rapidly growing subconfluent cell cultures were lysed in cold lysis buffer (50 mM Tris-HCl, pH 8.0, 100 mM NaCl, 3 mM EDTA, 1% Triton X-100 with a protease inhibitor cocktail). After 30 min incubation on ice with occasional mixing cell lysate was centrifuged at 10,000×rpm for 15 min at 4° C. The supernatant was carefully collected and stored at −70° C.

Extracellular matrix of KLN-205 cells was produced similarly like described by Langhofer et al. (1993). Subconfluent cell cultures were washed twice with PBS and incubated with 20 mM $NH_4OH$ for 10 min at room temperature. Immediately after incubation, cell culture dishes were washed with $H_2O$ and PBS to remove the disrupted cell material. The extracellular matrix was then solubilized into solubilization buffer (10 mM Tris pH 6.8, 8 M urea, 1% SDS, 5% β-mercaptoethanol) and stored at −70° C.

Samples of 50 μg of whole-cell extract and 50 μg of extracellular matrix were loaded per lane for electrophoreses on 7.5% SDS-PAGE gels (Bio-Rad) under reducing conditions and transferred to nitrocellulose membranes (Hybond P PVDF, Amersham Biosciences). Membranes were first probed with polyclonal antibodies for Pab-G12 (α3 chain), Pab-226 (β3 chain) and Pab-26 (γ2 chain), followed by peroxidase-labeled secondary anti-rabbit antibody (Bio-Rad) and visualized by the ECL system (Amersham Biosciences). Anti-β-Actin antibody (Novus Biologicals) was used as a loading control.

Histological analysis of A431 tumors. For immunohistological staining of the laminin α3, β3 and γ2 chains in A431 tumor tissue, mAb-7B2 (anti-α3), mAb-7B3 (anti-β3) and mAb-6C12 (anti-γ2) were used. For immunohistological staining of the laminin α3, β3 and γ2 chains in KLN-205 tumor tissue, Pab-G12 (anti-α3), Pab-226 (anti-β3) and Pab-26 (anti-γ2) were used. Staining of acetone-fixed frozen sections of 5 μm in thickness was carried out with the antibody, and species relevant IgG was used as a negative control. The sections were blocked for nonspecific binding with 1% BSA in PBS, and then incubated overnight at 4° C. with antibodies and controls diluted in PBS to 5-10 μg/ml. Subsequently, a biotinylated goat-anti-mouse antibody (Jackson Laboratories) or a biotinylated swine anti-rabbit antibody (DAKO) was applied, followed by horseradish peroxidase-avidin-biotin complex diluted as recommended by the manufacturer (Vectastain, Vector Laboratories). The color was developed in diaminobentsamidine (DAB), followed by counterstaining of the slides with hematoxylin. Polyclonal rabbit anti-human Ki67 antibody (Novus Biologicals, dilution 1:50) was used for the analysis of early tumors for proliferation. Staining of acetone-fixed frozen sections of 5 μm in thickness was carried out as described above. Light microscopy sections were visualized and photographed using an Olympus BX51 microscope. Immunofluorescent microscopy sections were visualized and photographed using a confocal laser scanning microscope Zeiss Axiovert 200M microscope with LSM 510 laser module.

Competition ELISA.

For competition ELISA, mAb-7B2 was biotinylated using a Sulfo-NHS-SS-biotin kit according to the manufacturer's instructions (Pierce Biotechnology, Inc). 96-well microtiter plates (Maxi-Sorpt™, Nunc) were coated o/n with 0.25 μg/well of rLM332 at 4° C. Potential non-specific binding was blocked with 1% BSA-PBS for 2 hours at room temperature (200 μl/well). 5 ng of biotinylated mAb7B2 and 500 ng of competitive antibodies and normal mouse IgG were mixed and pipetted to triplicate wells. After 30 minutes incubation, the wells were washed three times with PBS and horseradish peroxidase-avidin-biotin complex diluted as recommended by the manufacturer (Vectastain, Vector Laboratories). After 30 minutes incubation at room temperature, the color was developed in 2,2'-azino-bis-3-ethylbetzthiazoline-6-sulfonic acid (ABTS-peroxidase) substrate. Absorbance was read with a microtiter plate reader at 405 nm after 30 minutes.

Apoptosis Assays.

To study apoptosis in early A431 tumors in mice treated with mAb-7B2, BM165 and normal mouse IgG, tumor samples from days 7, 10 and 14 were prepared for TUNEL staining. 5 µm cryostat sections were fixed in 1% paraformaldehyde for 10 minutes at room temperature. Terminal deoxynucleotidyl transferase-mediated dUTP nick end labeling (TUNEL) staining was performed with the Apoptag Peroxidase Kit (Chemicon) and sections were counterstained with methyl green (Riedel de Haen). A total of 7-10 microscopic fields (400× magnification) from each section were randomly chosen and photographed. TUNEL-positive nuclei were counted using the analySIS Imaging software (Soft Imaging System GmbH).

The ability of mAb-7B2 to induce apoptosis of A431 cells grown on fibroblast matrix was measured by Annexin V-FITC apoptosis detection kit according to the manufacturer's instructions (Calbiochem). For the production of extracellular matrix produced by BJ fibroblasts flat-bottomed 12-well cell culture plates (Corning) were seeded with $2.5 \times 10^5$ cells/well of human BJ cells. Cells were cultured overnight to get a confluent cell culture. Fibroblast matrix was produced with 20 mM $NH_4OH$ as described earlier. Cell cultures were washed twice with PBS and incubated for 10 min at room temperature. Immediately after the production of matrix $2 \times 10^5$ cells/well of human A431 cells were seeded. The cells were allowed to attach for 5 hours before the addition of mAb-7B2 and control IgG (100 µg/ml). The cells were cultured for 16 hours before the analysis of apoptosis.

Microarrays.

$2 \times 10^5$ human A431 cells/well were seeded on freshly prepared fibroblast matrix and allowed to attach for 5 hours before the addition of a mixture of antibodies against all three LN-332 chains or control IgG (100 µg/ml). The cells were cultured for 16 hours before total RNA extraction (RNeasy Micro Kit, Qiagen).

For Affymetrix GeneChip analyses, the RNA was prepared according to the Expression Analysis Technical Manual. In essence, using 8 µg of total RNA as template, double-stranded DNA was synthesized by means of the One-cycle cDNA synthesis kit (Affymetrix) and T7-(dT)24 primer. The DNA was purified using GeneChip Sample Cleanup Module (Qiagen). In vitro transcription was performed to produce biotin labeled cRNA using an IVT labeling kit (Affymetrix). Biotinylated cRNA was cleaned with a GeneChip Sample Cleanup Module (Qiagen), fragmented to 35 to 200 nt, and hybridized to Affymetrix Human Genome U133 Plus 2 arrays containing approximately 55000 human transcripts. The array was stained with streptavidin-phycoerythrin (Molecular Probes), the staining signal was amplified by biotinylated anti-streptavidin (Vector Laboratories), and a second staining with streptavidin-phycoerythrin, and then scanned on GeneChip Scanner 3000. Signal intensities of the arrays were scaled to target value 500. Hybridization was performed using Affymetrix hybridization oven 640 (+45° C., 60 rpm, 16 hours). Washing and staining were performed using the Affymetrix Fluidics station 450 (EukGEWS2v5_450). Data analyses were performed using packages from the Bioconductor project (http://www.bioconductor.org). The affy package (version 1.12.2) was used to process the raw data. Statistic analysis with score package (version 1.6.0) was used for detecting differential gene expression between samples. It used probe level data directly to assess differences in gene expression. Gene Ontology annotation in the hgu133plus2 package (version 1.14.0) was used to extract all the probe sets related to certain biological categories.

Domain Specific Antibodies Against LN-332 Chains Used in this Study.

Polyclonal rabbit antibodies were prepared against the entire short arm (domains III-VI) of the β3 chain (Pab-226), as well as against domains III (Pab-1420) and V (Pab-1425) of the γ2 chain. mAbs 7B2 and 7E3 were prepared against the trimeric LN-332. mAb-7B2 was tested against all LN-332 fragments prepared in this study, and it only detected the G12 and G123 fragments of the α3 chain. mAb BM165 is a previously described antibody (Reference 27) made against the G domain of the α3 chain. Additionally, a polyclonal antibody Pab-BST was prepared against the whole trimeric recombinant human LN-332 molecule.

Supplementary Table 1

Differentially Expressed Genes Related to Apoptosis.

The probes related to apoptosis were identified using the Gene Ontology annotation in the hgu133plus2 package. The listed ratios were the log 2 transformed ratios between the anti-LN-332 antibody treated sample and the control. The p values were calculated using the sscore package. The genes are sorted according to the ratios.

| Probe Set ID | Gene Title | Symbol | log2 (treated/ control) | P-value |
|---|---|---|---|---|
| 222351_at | protein phosphatase 2 (formerly 2A), regulatory subunit A (PR 65), beta isoform | PPP2R1B | 4.32 | 0.04206 |
| 211298_s_at | albumin | ALB | 3.44 | 0.02537 |
| 236729_at | Caspase 3, apoptosis-related cysteine peptidase | CASP3 | 3.42 | 0.03432 |
| 231179_at | inositol hexaphosphate kinase 3 | IHPK3 | 3.25 | 0.02078 |
| 228269_x_at | Kv channel interacting protein 3, calsenilin | KCNIP3 | 3.09 | 0.01307 |
| 244836_at | Pleiomorphic adenoma gene-like 1 | PLAGL1 | 3.02 | 0.00601 |
| 211589_at | promyelocytic leukemia | PML | 2.76 | 0.00300 |
| 243127_x_at | deoxyribonuclease I | DNASE1 | 2.62 | 0.03216 |
| 232973_at | Dedicator of cytokinesis 1 | DOCK1 | 2.48 | 0.02428 |
| 1555454_at | lipopolysaccharide-induced TNF factor | LITAF | 2.33 | 0.04754 |
| 206324_s_at | death-associated protein kinase 2 | DAPK2 | 2.22 | 0.00221 |
| 203862_s_at | actinin, alpha 2 | ACTN2 | 2.16 | 0.04429 |

-continued

| Probe Set ID | Gene Title | Symbol | log2 (treated/ control) | P-value |
|---|---|---|---|---|
| 243314_at | Amyloid beta (A4) precursor protein (peptidase nexin-II, Alzheimer disease) | APP | 1.80 | 0.03316 |
| 241340_at | Caspase 4, apoptosis-related cysteine peptidase | CASP4 | 1.67 | 0.02722 |
| 213613_s_at | Cell division cycle 2-like 2 (PITSLRE proteins) | CDC2L2 | 1.63 | 0.01177 |
| 216776_at | B-cell receptor-associated protein 29 | BCAP29 | 1.58 | 0.02948 |
| 239251_at | Reticulon 4 | RTN4 | 1.56 | 0.00028 |
| 237133_at | Sterile alpha motif and leucine zipper containing kinase AZK | ZAK | 1.53 | 0.01551 |
| 206714_at | arachidonate 15-lipoxygenase, type B | ALOX15B | 1.48 | 0.04057 |
| 243509_at | B-cell translocation gene 1, anti-proliferative | BTG1 | 1.43 | 0.02041 |
| 2Q5859_at | lymphocyte antigen 86 | LY86 | 1.30 | 0.03873 |
| 213112_s_at | sequestosome 1 | SQSTM1 | 1.27 | 0.00441 |
| 236288_at | ring finger protein 34 | RNF34 | 1.15 | 0.00131 |
| 244803_at | Death associated protein 3 | DAP3 | 1.04 | 0.00229 |
| 239923_at | Forkhead box O3A | FOXO3A | 1.01 | 0.00285 |
| 208485_x_at | CASP8 and FADD-like apoptosis regulator | CFLAR | 0.99 | 0.01384 |
| 215834_x_at | scavenger receptor class B, member 1 | SCARB1 | 0.91 | 0.03621 |
| 222380_s_at | Programmed cell death 6 | PDCD6 | 0.89 | 0.00158 |
| 215067_x_at | peroxiredoxin 2 | PRDX2 | 0.87 | 0.03848 |
| 225656_at | EF-hand domain (C-terminal) containing 1 | EFHC1 | 0.87 | 0.00000 |
| 223746_at | serine/threonine kinase 4 | STK4 | 0.84 | 0.01960 |
| 214329_x_at | tumor necrosis factor (ligand) superfamily, member 10 | TNFSF10 | 0.82 | 0.00001 |
| 214617_at | perforin 1 (pore forming protein) | PRF1 | 0.81 | 0.01622 |
| 1557675_at | V-raf-1 murine leukemia viral oncogene homolog 1 | RAF1 | 0.78 | 0.03532 |
| 219423_x_at | tumor necrosis factor receptor superfamily, member 25 | TNFRSF25 | 0.72 | 0.00000 |
| 1556385_at | Cardiotrophin-like cytokine factor 1 | CLCF1 | 0.72 | 0.00002 |
| 221833_at | Peroxisomal LON protease like | LONPL | 0.70 | 0.00012 |
| 206467_x_at | tumor necrosis factor receptor superfamily, member 6b, decoy | TNFRSF6B | 0.68 | 0.01154 |
| 235711_at | purine-rich element binding protein B | PURB | 0.68 | 0.02917 |
| 226798_at | BCL2-like 13 (apoptosis facilitator) | BCL2L13 | 0.65 | 0.01766 |
| 1552701_a_at | caspase-1 dominant-negative inhibitor pseudo-ICE | COP1 | 0.65 | 0.00074 |
| 205976_at | KIAA0971 | KIAA0971 | 0.63 | 0.00831 |
| 202284_s_at | cyclin-dependent kinase inhibitor 1A (p21, Cip1) | CDKN1A | 0.62 | 0.00008 |
| 204891_s_at | lymphocyte-specific protein tyrosine kinase | LCK | 0.62 | 0.00000 |
| 37152_at | peroxisome proliferative activated receptor, delta | PPARD | 0.62 | 0.00003 |
| 222514_at | Ras-related GTP binding C | RRAGC | 0.61 | 0.01896 |
| 1729_at | TNFRSFIA-associated via death domain | TRADD | 0.61 | 0.00003 |
| 201841_s_at | heat shock 27 kDa protein 1 | HSPB1 | 0.59 | 0.00019 |
| 211492_s_at | adrenergic, alpha-1A-, receptor | ADRA1A | 0.59 | 0.02941 |
| 209723_at | serpin peptidase inhibitor, clade B (ovalbumin), member 9 | SERPINB9 | 0.59 | 0.00831 |
| 208835_s_at | cisplatin resistance-associated overexpressed protein | CROP | −0.61 | 0.00000 |
| 203372_s_at | suppressor of cytokine signaling 2 | SOCS2 | −0.62 | 0.00158 |
| 204656_at | Src homology 2 domain containing adaptor protein B | SHB | −0.66 | 0.02205 |
| 239226_at | Rhotekin | RTKN | −0.81 | 0.00033 |
| 228121_at | Transforming growth factor, beta 2 | TGFB2 | −0.81 | 0.00001 |
| 213468_at | excision repair cross-complementing rodent repair deficiency, complementation group 2 | ERCC2 | −0.81 | 0.03152 |
| 225877_at | trypsin domain containing 1 | TYSND1 | −0.82 | 0.02923 |
| 216127_at | protein disulfide isomerase family A, member 2 | PDIA2 | −0.90 | 0.02051 |
| 210234_at | glutamate receptor, metabotropic 4 | GRM4 | −0.92 | 0.00643 |
| 244810_at | TRIAD3 protein | TRIAD3 | −0.95 | 0.00868 |
| 1556806_at | Death-associated protein | DAP | −1.00 | 0.03940 |
| 220451_s_at | baculoviral IAP repeat-containing 7 (livin) | BIRC7 | −1.12 | 0.00703 |

-continued

| Probe Set ID | Gene Title | Symbol | log2 (treated/control) | P-value |
|---|---|---|---|---|
| 205291_at | interleukin 2 receptor, beta | IL2RB | −1.45 | 0.04517 |
| 232546_at | tumor protein p73 | TP73 | −1.53 | 0.01057 |
| 206341_at | interleukin 2 receptor, alpha | IL2RA | −1.70 | 0.03660 |
| 208381_s_at | sphingosine-1-phosphate lyase 1 | SGPL1 | −1.91 | 0.00986 |
| 205426_s_at | huntingtin interacting protein 1 | HIP1 | −2.01 | 0.00866 |
| 206977_at | parathyroid hormone | PTH | −2.36 | 0.04583 |
| 207634_at | programmed cell death 1 | PDCD1 | −2.44 | 0.00888 |
| 207816_at | lactalbumin, alpha- | LALBA | −2.86 | 0.00188 |
| 208000_at | GPI anchored molecule like protein | GML | −2.88 | 0.01891 |
| 210708_x_at | caspase 10, apoptosis-related cysteine peptidase | CASP10 | −3.14 | 0.00919 |
| 217088_s_at | natural cytotoxicity triggering receptor 1 | NCR1 | −3.37 | 0.01640 |
| 214935_at | nucleoporin 62 kDa | NUP62 | −3.62 | 0.03822 |
| 1555349_a_at | integrin, beta 2 (complement component 3 receptor 3 and 4 subunit) | ITGB2 | −3.73 | 0.00270 |
| 1568768_s_at | brain and reproductive organ-expressed (TNFRSF1A modulator) | BRE | −3.87 | 0.00867 |
| 222073_at | collagen, type IV, alpha 3 (Goodpasture antigen) | COL4A3 | −5.53 | 0.01789 |

REFERENCES

1. Aumailley M, Bruckner-Tuderman L, Carter W G, Deutzmann R, Edgar D, Ekblom P, Engel J, Engvall E, Hohenester E, Jones J C, Kleinman H K, Marinkovich M P et al. A simplified laminin nomenclature. Matrix Biol 2005; 24:326-32.
2. Miner J H, Yurchenco P D. Laminin functions in tissue morphogenesis. Annu Rev Cell Dev Biol 2004; 20:255-84.
3. Kallunki P, Sainio K, Eddy R, Byers M, Kallunki T, Sariola H, Beck K, Hirvonen H, Shows T B, Tryggvason K. A truncated laminin chain homologous to the B2 chain: structure, spatial expression, and chromosomal assignment. J Cell Biol 1992; 119:679-93.
4. Gerecke D R, Wagman D W, Champliaud M F, Burgeson R E. The complete primary structure for a novel laminin chain, the laminin B1k chain. J Biol Chem 1994; 269: 11073-80.
5. Ryan M C, Tizard R, VanDevanter D R, Carter W G. Cloning of the LamA3 gene encoding the alpha 3 chain of the adhesive ligand epiligrin. Expression in wound repair. J Biol Chem 1994; 269:22779-87.
6. Aberdam D, Galliano M F, Vailly J, Pulkkinen L, Bonifas J, Christiano A M, Tryggvason K, Uitto J, Epstein Jr E H, Ortonne J P, Meneguzzi G. Herlitz's junctional epidermolysis bullosa is linked to mutations in the gene (LAMC2) for the gamma 2 subunit of nicein/kalinin (LAMININ-5). Nat Genet 1994; 6:299304.
7. Pulkkinen L, Christiano A M, Airenne T, Haakana H, Tryggvason K, Uitto J. Mutations in the gamma 2 chain gene (LAMC2) of kalinin/laminin 5 in the junctional forms of epidermolysis bullosa. Nat Genet 1994; 6:293-7.
8. Pulkkinen L, Uitto J. Mutation analysis and molecular genetics of epidermolysis bullosa. Matrix Biol 1999; 18:29-42.
9. Salo S, Haakana H, Kontusaari S, Hujanen E, Kallunki T, Tryggvason K. Laminin-5 promotes adhesion and migration of epithelial cells: identification of a migration-related element in the gamma2 chain gene (LAMC2) with activity in transgenic mice. Matrix Biol 1999; 18:197-210.
10. Nguyen B P, Gil S G, Carter W G. Deposition of laminin 5 by keratinocytes regulates integrin adhesion and signaling. J Biol Chem 2000; 275:31896-907.
11. Carter W G, Ryan M C, Gahr P J. Epiligrin, a new cell adhesion ligand for integrin alpha 3 beta 1 in epithelial basement membranes. Cell 1991; 65:599-610.
12. Hanks S K, Calalb M B, Harper M C, Patel S K. Focal adhesion protein-tyrosine kinase phosphorylated in response to cell attachment to fibronectin. Proc Natl Acad Sci USA 1992; 89:8487-91.
13. Shang M, Koshikawa N, Schenk S, Quaranta V. The LG3 module of laminin-5 harbors a binding site for integrin alpha3beta1 that promotes cell adhesion, spreading, and migration. J Biol Chem 2001; 276:33045-53.
14. Rousselle P, Keene D R, Ruggiero F, Champliaud M F, Rest M, Burgeson R E. Laminin 5 binds the NC-1 domain of type VII collagen. J Cell Biol 1997; 138:719-28.
15. Pyke C, Rømer J, Kallunki P, Lund L R, Ralfkiaer E, Danø K, Tryggvason K. The gamma 2 chain of kalinin/laminin 5 is preferentially expressed in invading malignant cells in human cancers. Am J Pathol 1994; 145:782-91.
16. Pyke C, Salo S, Ralfkiaer E, Romer J, Dano K, Tryggvason K. Laminin-5 is a marker of invading cancer cells in some human carcinomas and is coexpressed with the receptor for urokinase plasminogen activator in budding cancer cells in colon adenocarcinomas. Cancer Res 1995; 55:4132-9.
17. Sordat I, Bosman F T, Dorta G, Rousselle P, Aberdam D, Blum A L, Sordat B. Differential expression of laminin-5 subunits and integrin receptors in human colorectal neoplasia. J Pathol 1998; 185:44-52.
18. Koshikawa N, Moriyama K, Takamura H, Mizushima H, Nagashima Y, Yanoma S, Miyazaki K. Overexpression of laminin gamma2 chain monomer in invading gastric carcinoma cells. Cancer Res 1999; 59:5596-601.
19. Skyldberg B, Salo S, Eriksson E, Aspenblad U, Moberger B, Tryggvason K, Auer G. Laminin-5 as a marker of invasiveness in cervical lesions. J Natl Cancer Inst 1999; 91:1882-7.
20. Miyazaki K, Kikkawa Y, Nakamura A, Yasumitsu H, Umeda M. A large cell-adhesive scatter factor secreted by human gastric carcinoma cells. Proc Natl Acad Sci USA 1993; 90:11767-71.
21. Fukushima Y, Ohnishi T, Arita N, Hayakawa T, Sekiguchi K. Integrin alpha3beta1-mediated interaction with lami- 21. nin-5 stimulates adhesion, migration and invasion of malignant glioma cells. Int J Cancer 1998; 76:63-72.
22. Hao J, Yang Y, McDaniel K M, Dalkin B L, Cress A E, Nagle R B. Differential expression of laminin 5 (alpha 3 beta 3 gamma 2) by human malignant and normal prostate. Am J Pathol 1996; 149:1341-9.
23. Martin K J, Kwan C P, Nagasaki K, Zhang X, O'Hare M J, Kaelin C M, Burgeson R E, Pardee A B, Sager R. Down-regulation of laminin-5 in breast carcinoma cells. Mol Med 1998; 4:602-13.
24. Mizushima H, Hirosaki T, Miyata S, Takamura H, Miyagi Y, Miyazaki K. Expression of laminin-5 enhances tumorigenicity of human fibrosarcoma cells in nude mice. Jpn J Cancer Res 2002; 93:652-9.
25. Dajee M, Lazarov M, Zhang J Y, Cai T, Green C L, Russell A J, Marinkovich M P, Tao S, Lin Q, Kubo Y, Khavari P A. NF-kappaB blockade and oncogenic Ras trigger invasive human epidermal neoplasia. Nature 2003; 421:639-43.
26. Stoltzfus P, Salo S, Eriksson E, Aspenblad U, Tryggvason K, Auer G, Avall-Lundqvist E. Laminin-5 gamma2 chain expression facilitates detection of invasive squamous cell carcinoma of the uterine cervix. Int J Gynecol Pathol 2004; 23:215-22.
27. Marinkovich M P, Lunstrum G P, Keene D R, Burgeson R E. The dermal-epidermal junction of human skin contains a novel laminin variant. J Cell Biol 1992; 119:695-703.
28. Baker S E, DiPasquale A P, Stock E L, Quaranta V, Fitchmun M, Jones J C. Morphogenetic effects of soluble laminin-5 on cultured epithelial cells and tissue explants. Exp Cell Res 1996; 228:262-70.
29. Gonzales M, Haan K, Baker S E, Fitchmun M, Todorov I, Weitzman S, Jones J C. A cell signal pathway involving laminin-5, alpha3beta1 integrin, and mitogenactivated protein kinase can regulate epithelial cell proliferation. Mol Biol Cell 1999; 10:259-70.
30. Solly K, Wang X, Xu X, Strulovici B, Zheng W. Application of real-time cell electronic sensing (RT-CES) technology to cell-based assays. Assay Drug Dev Technol 2004; 2:363-72.
31. Glamann J, Hansen A J. Dynamic detection of natural killer cell-mediated cytotoxicity and cell adhesion by electrical impedance measurements. Assay Drug Dev Technol 2006; 4:555-63.
32. Langhofer M, Hopkinson S B, Jones J C. The matrix secreted by 804G cells contains laminin-related components that participate in hemidesmosome assembly in vitro. J Cell Sci 1993; 105 (Pt 3):753-64.
33. Levkau B, Koyama H, Raines E W, Clurman B E, Herren B, Orth K, Roberts J M, Ross R. Cleavage of p21Cip1/Waf1 and p27Kip1 mediates apoptosis in endothelial cells through activation of Cdk2: role of a caspase cascade. Mol Cell 1998; 1:553-63.
34. Park J A, Kim K W, Kim S I, Lee S K. Caspase 3 specifically cleaves p21WAF1/CIP1 in the earlier stage of apoptosis in SK-HEP-1 human hepatoma cells. Eur J Biochem 1998; 257:242-8.
35. Zhang Y, Fujita N, Tsuruo T. Caspase-mediated cleavage of p21Waf1/Cip1 converts cancer cells from growth arrest to undergoing apoptosis. Oncogene 1999; 18:1131-8.
36. Mizushima H, Miyagi Y, Kikkawa Y, Yamanaka N, Yasumitsu H, Misugi K, Miyazaki K. Differential expression of laminin-5/ladsin subunits in human tissues and cancer cell lines and their induction by tumor promoter and growth factors. J Biochem (Tokyo) 1996; 120:1196-202.
37. Berndt A, Hyckel P, Konneker A, Katenkamp D, Kosmehl H. Oral squamous cell carcinoma invasion is associated with a laminin-5 matrix re-organization but independent of basement membrane and hemidesmosome formation. clues from an in vitro invasion model. Invasion Metastasis 1997; 17:251-8.
38. Nordemar S, Kronenwett U, Auer G, Högmo A, Lindholm J, Edström S, Tryggvasson K, Linder S, Munck-Wikland E. Laminin-5 as a predictor of invasiveness in cancer in situ lesions of the larynx. Anticancer Res 2001; 21:50912.
39. Giannelli G, Fransvea E, Bergamini C, Marinosci F, Antonaci S. Laminin-5 chains are expressed differentially in metastatic and nonmetastatic hepatocellular carcinoma. Clin Cancer Res 2003; 9:3684-91.
40. Marinkovich M P. Tumour microenvironment: laminin 332 in squamous-cell carcinoma. Nat Rev Cancer 2007; 7:370-80.
41. Frank D E, Carter W G. Laminin 5 deposition regulates keratinocyte polarization and persistent migration. J Cell Sci 2004; 117:1351-63.
42. Choma D P, Pumiglia K, DiPersio C M. Integrin alpha3beta1 directs the stabilization of a polarized lamellipodium in epithelial cells through activation of Rac1. J Cell Sci 2004; 117:3947-59.
43. Utani A, Nomizu M, Yamada Y. Fibulin-2 binds to the short arms of laminin-5 and laminin-1 via conserved amino acid sequences. J Biol Chem 1997; 272:2814-20.
44. Decline F, Rousselle P. Keratinocyte migration requires alpha2beta1 integrinmediated interaction with the laminin 5 gamma2 chain. J Cell Sci 2001; 114:81123.
45. Sasaki T, Gohring W, Mann K, Brakebusch C, Yamada Y, Fässler R, Timpl R. Short arm region of laminin-5 gamma2 chain: structure, mechanism of processing and binding to heparin and proteins. J Mol Biol 2001; 314:751-63.
46. Ogawa T, Tsubota Y, Hashimoto J, Kariya Y, Miyazaki K. The short arm of laminin gamma2 chain of laminin-5 (laminin-332) binds syndecan-1 and regulates cellular adhesion and migration by suppressing phosphorylation of integrin beta4 chain. Mol Biol Cell 2007; 18:1621-33.
47. Condeelis J S, Wyckoff J B, Bailly M, Pestell R, Lawrence D, Backer J, Segall J E. Lamellipodia in invasion. Semin Cancer Biol 2001; 11:119-28.
48. Pollard T D, Borisy G G. Cellular motility driven by assembly and disassembly of actin filaments. Cell 2003; 112:453-65.
49. Bailly M, Condeelis J. Cell motility: insights from the backstage. Nat Cell Biol 2002; 4:E292-4.
50. Goldfinger L E, Hopkinson S B, deHart G W, Collawn S, Couchman J R, Jones J C. The alpha3 laminin subunit, alpha6beta4 and alpha3beta1 integrin coordinately regulate wound healing in cultured epithelial cells and in the skin. J Cell Sci 1999; 112 (Pt 16):2615-29.
51. Ortiz-Urda S, Garcia J, Green C L, Chen L, Lin Q, Veitch D P, Sakai L Y, Lee H, Marinkovich M P, Khavari P A. Type VII collagen is required for Ras-driven human epidermal tumorigenesis. Science 2005; 307:1773-6.
52. Waterman E A, Sakai N, Nguyen N T, Horst B A, Veitch D P, Dey C N, Ortiz-Urda S, Khavari P A, Marinkovich M P. A laminin-collagen complex drives human epidermal carcinogenesis through phosphoinositol-3-kinase activation. Cancer Res 2007; 67:4264-70.
53. Yuen H W, Ziober A F, Gopal P, Nasrallah I, Falls E M, Meneguzzi G, Ang H Q, Ziober B L. Suppression of laminin-5 expression leads to increased motility, tumorigenicity, and invasion. Exp Cell Res 2005; 309:198-210.
54. Frisch S M, Screaton R A. Anoikis mechanisms. Curr Opin Cell Biol 2001; 13:555-62.
55. Stupack D G, Cheresh D A. Get a ligand, get a life: integrins, signaling and cell survival. J Cell Sci 2002; 115: 3729-38.

56. Kodama K, Ishii G, Miyamoto S, Goya M, Zhang S C, Sangai T, Yoshikawa T, Hasebe T, Hitomi Y, Izumi K, Ochiai A. Laminin 5 expression protects against anoikis at aerogenous spread and lepidic growth of human lung adenocarcinoma. Int J Cancer 2005; 116:876-84.

57. Woodhouse E C, Chuaqui R F, Liotta L A. General mechanisms of metastasis. Cancer 1997; 80:1529-37.

58. Atsumi N, Ishii G, Kojima M, Sanada M, Fujii S, Ochiai A. Podoplanin, a novel marker of tumor-initiating cells in human squamous cell carcinoma A431. Biochem Biophys Res Commun. 2008; 373:36-41.

The compositions and methods of the present disclosure have been described with reference to the preferred embodiments. Obviously, modifications and alterations will occur to others upon reading and understanding the preceding detailed description. It is intended that this disclosure be construed as including all such modifications and alterations insofar as they come within the scope of the appended claims or the equivalents thereof.

The invention claimed is:

1. A composition comprising antibodies against domains III-VI on the β3 chain of laminin-332.

2. The composition of claim 1, further comprising antibodies against the γ2 chain of laminin-332.

3. The composition of claim 2, wherein the antibodies against the γ2 chain bind to domain III or domain V on the γ2 chain.

4. The composition of claim 1, further comprising antibodies against the G domain of the α3 chain of laminin-332.

5. The composition of claim 4, wherein the antibodies against the G domain bind to subdomains G1-G3 of the α3 chain.

6. The composition of claim 1, further comprising antibodies against the γ2 chain of laminin-332 and antibodies against the G domain of the α3 chain of laminin-332.

7. A method of decreasing cell migration of cells secreting laminin-332 and exhibiting metastasis, comprising contacting cells with antibodies against domains III-VI on the β3 chain of laminin-332.

8. A method of claim 7, further comprising antibodies against the γ2 chain of laminin-332.

9. The method of claim 8, wherein the antibodies against the γ2 chain bind to domain III or domain V on the γ2 chain.

10. The method of claim 7, further comprising antibodies against the G domain of the α3 chain of laminin-332.

11. The method of claim 10, wherein the antibodies against the G domain bind to subdomains G1-G3 of the α3 chain.

12. The method of claim 7, further comprising antibodies against the γ2 chain of laminin-332 and antibodies against the G domain of the α3 chain of laminin-332.

13. A method of decreasing tumor growth, comprising administering to a subject with a laminin-332 secreting tumor an effective amount of an antibody against domains III-VI on the β3 chain of laminin-332.

14. The method of claim 13, further comprising antibodies against the γ2 chain of laminin-332.

15. The method of claim 13, further comprising antibodies against the G domain of α3 chain of laminin-332.

16. The method of claim 15, wherein the antibodies against the G domain bind to subdomains G1-G3 of the α3 chain.

17. The method of claim 13, further comprising antibodies against the γ2 chain of laminin-332 and antibodies against the G domain of the α3 chain of laminin-332.

18. The composition of claim 2, wherein the antibodies against the γ2 chain bind to domain III or domain V on the γ2 chain and the composition further includes antibodies against the G1-G3 subdomains of the α3 chain of laminin-332.

19. The method of claim 8, wherein the antibodies against the γ2 chain bind to domain III or domain V on the γ2 chain and the method further includes contacting cells with antibodies against the G1-G3 subdomains of the α3 chain of laminin-332.

20. The method of claim 14, wherein the antibodies against the γ2 chain bind to domain III or domain V on the γ2 chain and the method further includes administering to the subject antibodies against the G1-G3 subdomains of the α3 chain of laminin-332.

* * * * *

UNITED STATES PATENT AND TRADEMARK OFFICE
CERTIFICATE OF CORRECTION

PATENT NO. : 8,545,845 B2
APPLICATION NO. : 13/060358
DATED : October 1, 2013
INVENTOR(S) : Tryggvason et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 300 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 13

<210> SEQ ID NO 1
<211> LENGTH: 19
<212> TYPE: DNA
<213> ORGANISM: Mus musculus

<400> SEQUENCE: 1
cagtcaggac ccaagggtg                                              19

<210> SEQ ID NO 2
<211> LENGTH: 18
<212> TYPE: DNA
<213> ORGANISM: Mus musculus

<400> SEQUENCE: 2
tatccgcagc ataaccgg                                               18

<210> SEQ ID NO 3
<211> LENGTH: 15
<212> TYPE: DNA
<213> ORGANISM: Mus musculus

<400> SEQUENCE: 3
tcatctccgc ccctt                                                  15

<210> SEQ ID NO 4
<211> LENGTH: 16
<212> TYPE: DNA
<213> ORGANISM: Mus musculus

<400> SEQUENCE: 4
aacacggaag gccatg                                                 16

<210> SEQ ID NO 5
<211> LENGTH: 21
<212> TYPE: DNA
<213> ORGANISM: Homo sapiens

<400> SEQUENCE: 5
gctagccctg gaagatttga a                                           21

<210> SEQ ID NO 6
<211> LENGTH: 25
<212> TYPE: DNA
<213> ORGANISM: Homo sapiens

<400> SEQUENCE: 6
atcgatcagg gaagtggtga gcaag                                       25

<210> SEQ ID NO 7
<211> LENGTH: 27

```
<212> TYPE: DNA
<213> ORGANISM: Homo sapiens

<400> SEQUENCE: 7
atcgatcaca caagcttcca gtcttcc                                          27

<210> SEQ ID NO 8
<211> LENGTH: 19
<212> TYPE: DNA
<213> ORGANISM: Homo sapiens

<400> SEQUENCE: 8
ggctacttcg gggaccatt                                                   19

<210> SEQ ID NO 9
<211> LENGTH: 21
<212> TYPE: DNA
<213> ORGANISM: Homo sapiens

<400> SEQUENCE: 9
tgcaaacaca ggtgccatca c                                                21

<210> SEQ ID NO 10
<211> LENGTH: 24
<212> TYPE: DNA
<213> ORGANISM: Homo sapiens

<400> SEQUENCE: 10
cagacaagtg tcgagcttgc aact                                             24

<210> SEQ ID NO 11
<211> LENGTH: 20
<212> TYPE: DNA
<213> ORGANISM: Homo sapiens

<400> SEQUENCE: 11
gtggctgacc atgtcttcct                                                  20

<210> SEQ ID NO 12
<211> LENGTH: 19
<212> TYPE: DNA
<213> ORGANISM: Homo sapiens

<400> SEQUENCE: 12
ccaccaggtc ctgggactt                                                   19

<210> SEQ ID NO 13
<211> LENGTH: 23
<212> TYPE: DNA
<213> ORGANISM: Homo sapiens

<400> SEQUENCE: 13
tgtccccaag gtctgcatcc tga                                              23
```